(12) United States Patent
Wu et al.

(10) Patent No.: US 8,383,880 B2
(45) Date of Patent: Feb. 26, 2013

(54) INFERTILITY CONTROL OF GENETICALLY MODIFIED FISH

(75) Inventors: Jen-Leih Wu, Taipei (TW); Shao-Yang Hu, Changhua (TW); Guor Mour Her, Keelung (TW)

(73) Assignees: Academia Sinica, Taipei (TW); National Taiwan Ocean University, Keelung (TW)

( * ) Notice: Subject to any disclaimer, the term of this patent is extended or adjusted under 35 U.S.C. 154(b) by 288 days.

(21) Appl. No.: 12/705,509

(22) Filed: Feb. 12, 2010

(65) Prior Publication Data

US 2010/0212039 A1 Aug. 19, 2010

Related U.S. Application Data

(60) Provisional application No. 61/153,519, filed on Feb. 18, 2009.

(51) Int. Cl.
*A01K 67/027* (2006.01)
*C12N 15/00* (2006.01)

(52) U.S. Cl. ............... 800/20; 800/21; 800/22

(58) Field of Classification Search ............... 800/3, 20, 800/21, 22
See application file for complete search history.

(56) References Cited

U.S. PATENT DOCUMENTS 7,525,011 B2 * 4/2009 Look et al. .................. 800/20

OTHER PUBLICATIONS

Curado et al., Nitroreductase-mediated cell/tissue ablation in zebrafish: a spatially and temporally controlled ablation method with applications in developmental and regeneration studies Nat Protoc. 2008; 3(6): 948-954.*
Sun Shu-na et al., 2009; Fudan University, Shanghai 200032, China, Cardiovascular Center, Children's Hospital the effects of folic acid deficiency on the axial development of zebrafish 36 (6): 663-669 Abstract.*
Freeman et al., (Comparative Biochemistry and Physiology Part B, Biochemistry, 1983, pp. 27-30; Methemoglobin reductase activity in phylogenetically diverse piscine species Abstract.*
Iwata et al., (1990, J Biochem. Feb. 1990;107(2):209-12, Immunological and enzymological localization of carbonyl reductase in ovary and liver of various species.abstract.*
Liu et al., Biol Reprod. Jun. 2006;74(6):1016-25. Epub Feb. 15, 2006.Tandem-repeated Zebrafish zp3 genes possess oocyte-specific promoters and are insensitive to estrogen induction.*
Pisharath et al., Comp Med. Jun. 2007;57(3):241-6. Validation of nitroreductase, a prodrug-activating enzyme, mediated cell death in embryonic zebrafish (*Danio rerio*).*
Chia-Chun Hsu et al. (2009) "Inducible Male Infertility by Targeted Cell Ablation in Zebrafish Testis" Marine Biotechnol, Springer New York, DOI 10.1007/s10126-009-9248-4.
Shao-Yang Hu et al., "Nitroreductase-mediated Gonadal Dysgenesis for Infertility Control of Genetically Modified Zebrafish" Mar Biotechnol DOI 10.1007/s10126-009-9244-8, 2008.
Bulina et al. (2006), "Chromophore-assisted light inactivation (CALI) using the phototoxic fluorescent protein KillerRed" Nature Protocols, vol. 1, No. 2, 947-953.
Bulina et al., "A genetically encoded photosensitizer" (2006) Nature, Biotechnology vol. 24, No. 1, 95-99.
Pletnev et al., (2009) "Structural Basis for Phototoxicity of the Genetically Encoded Photosensitizer KillerRed" The Journal of Biological Chemistry vol. 284, No. 46, pp. 32028-32039.

* cited by examiner

*Primary Examiner* — Maria Leavitt
(74) *Attorney, Agent, or Firm* — Hsiu-Ming Saunders; Intellectual Property Connections, Inc.

(57) ABSTRACT

A method of inducing male and/or female infertility in a genetically modified (GM) fish is disclosed. Also disclosed is a method of generating an infertile GM fish with a phenotype and/or genotype of interest. The method involves generation of a GM fish whose genome comprises a foreign transgene operably linked to a fish gonad-specific promoter selected from the group consisting of an ovary-specific promoter and a testis-specific promoter. The transgene comprises a suicide gene selected from the group consisting of a reductase and a photosensitizer, in which the reductase is operably linked to a reporter gene. Infertility of the GM fish is induced if the GM fish expressing the reductase is treated with an effective amount of a reductase-activated cytotoxic prodrug or if the GM fish expressing the photosensitizer is treated with light irradiation.

17 Claims, 12 Drawing Sheets

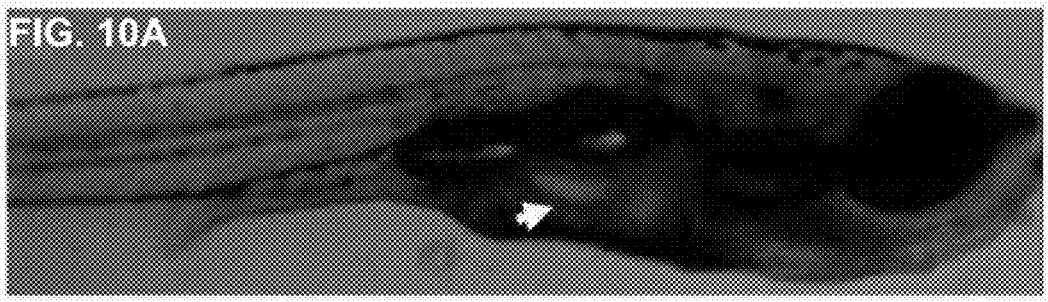
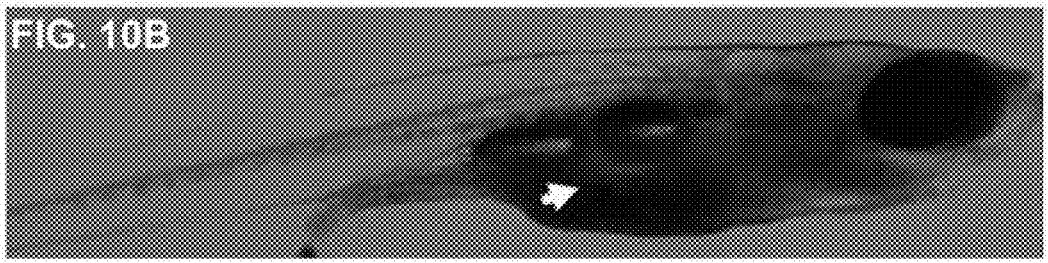
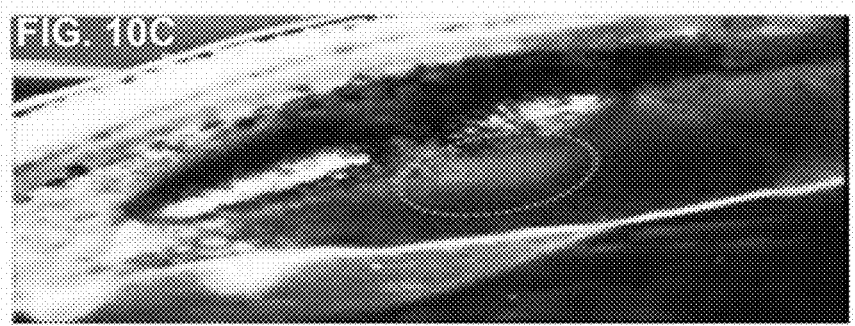

FIG. 11B
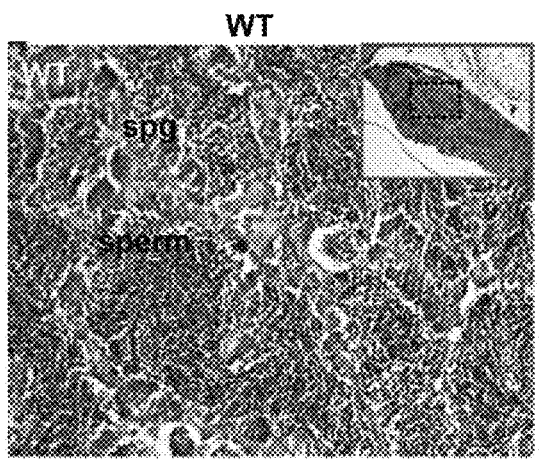
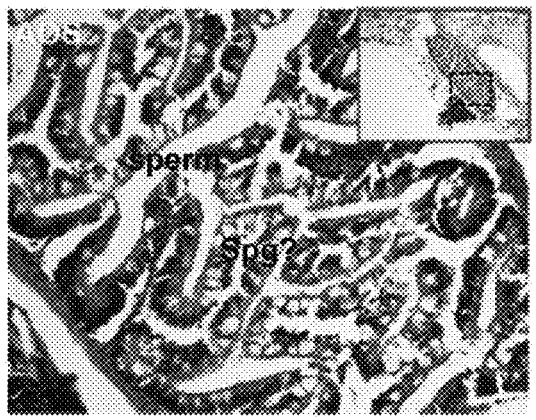
FIG. 11C
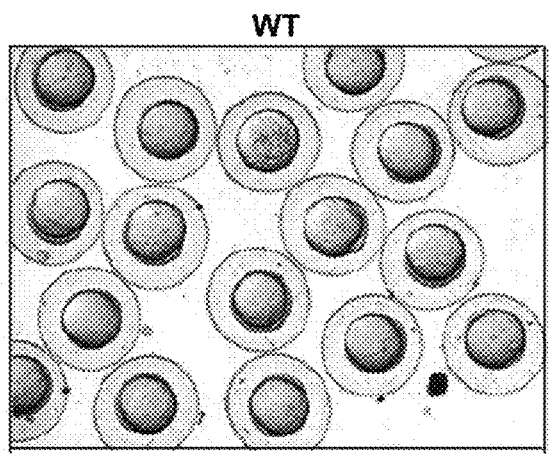
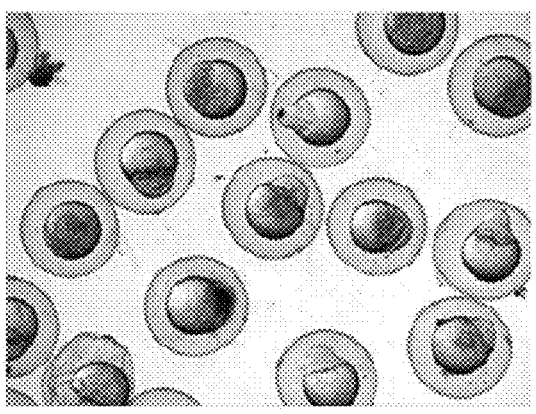

INFERTILITY CONTROL OF GENETICALLY MODIFIED FISH

REFERENCE TO RELATED APPLICATION

The present application claims the priority to U.S. Provisional Application Ser. No. 61/153,519, filed Feb. 18, 2009, which is herein incorporated by reference in its entirety.

FIELD OF THE INVENTION

The present invention relates generally to genetically modified (GM) fish, and more specifically to inducible infertility in GM fish.

BACKGROUND OF THE INVENTION

The main impediment to the commercialization of genetically modified (GM) fish is the incomplete assessment of food safety and the ecological impacts. The ecological impacts encompass global issues concerning gene flow and the escape of transgenic fish, which may pose a threat to wild natural fish stocks. Infertility control may be a core technology to solve the potential problem of GM fish release into the natural environment. The traditional approach to infertility control in GM fish is polyploidy technology. This technology causes infertility by changing the number of chromosomes in an individual. Temperature-shock or pressure-stress treatment of freshly fertilized fish eggs to induce triploidy is another common practice for infertility, but unfortunately triploid infertility is rarely 100% effective. An alternative method to induce infertility in fish is the blockade of gonadotropin releasing hormone (GnRH) expression by antisense RNA, ribozymes, or siRNA. However, although undeveloped or deficient gonads result from a knockdown of GnRH, the presence of antisense GnRH in fish do not result in 100% infertility. Furthermore, even if such a treatment was successful in achieving 100% infertility, the transgenic stocks with superior characteristics are not heritable. For this reason, infertility would need to be inducible; otherwise this infertility would be equivalent to 'killing the goose that lays the golden eggs'.

Therefore, a heretofore unaddressed need exists in the art to address the aforementioned deficiencies and inadequacies, especially in connection with establishing a platform technology for inducible infertility in GM fish.

SUMMARY OF THE INVENTION

In one aspect, the invention relates to a GM fish whose genome comprises:
  (a) a fish gonad-specific promoter; and
  (b) a foreign transgene operably linked to the fish gonad-specific promoter, in which the foreign transgene comprises a suicide gene selected from the group consisting of a reductase and a photosensitizer;
wherein the reductase is operably linked to a reporter gene; and further wherein the fish gonad-specific promoter is selected from the group consisting of a fish ovary-specific promoter and a fish testis-specific promoter; and wherein the female of the fish expresses the transgene that is operably linked to the ovary-specific promoter in the ovary of the fish, and the male of the fish expresses the transgene that is operably linked to the testis-specific promoter; and further wherein infertility of the GM fish is induced and/or the probability of infertility of the GM fish is increased as compared to that of a wild-type counterpart if the GM fish expressing the reductase is treated with an effective amount of a reductase-activated cytotoxic prodrug, or if the GM fish expressing the photosensitizer is treated with light irradiation.

In another aspect, the invention relates to a genetically modified (GM) fish whose genome comprises a fusion transgene operably linked to a fish gonad-specific promoter, wherein the fusion transgene comprises:
  (a) a foreign reductase-encoding gene; and
  (b) a reporter gene operably linked to the reductase-encoding gene;
wherein the fish gonad-specific promoter is selected from the group consisting of a fish ovary-specific promoter and a fish testis-specific promoter; and wherein the female of the fish expresses the fusion transgene that is operably linked to the ovary-specific promoter in the ovary of the fish, and the male of the fish expresses the fusion transgene that is operably linked to the testis-specific promoter, and further wherein infertility of the GM fish is induced and/or the probability of infertility of the GM fish is increased as compared to that of a wild-type counterpart if the GM fish expressing the fusion transgene is treated with an effective amount of a reductase-activated cytotoxic prodrug.

In another aspect, the invention relates to a progeny of the aforementioned GM fish, in which the progeny exhibits the expression of the transgene in the gonad thereof.

In another aspect, the invention relates to a GM fish progeny, whose maternal parent is a homozygous female of the aforementioned GM fish with a fish ovary-specific promoter operably linked to the fusion transgene, and paternal parent a homozygous male transgenic fish with a phenotype and/or genotype of interest, wherein the GM fish progeny exhibits the expression of the fusion gene in the gonad thereof and manifests the phenotype and/or genotype of interest.

Further in another aspect, the invention relates to a GM fish progeny of a homozygous male and homozygous female of the aforementioned GM fish with a fish testis-specific promoter operably linked to the fusion transgene, in which the homozygous male of the aforementioned GM fish exhibits an increased probability of infertility as compared to that of a wild-type counterpart if treated with a therapeutically effective amount of a reductase-activated cytotoxic prodrug.

Further in another aspect, the invention relates to a GM fish whose genome comprises at least two copies of a fusion transgene with each copy operably linked to a different fish testis-specific promoter, wherein the fusion transgene comprises:
  (a) a foreign reductase-encoding gene; and
  (b) a reporter gene operably linked to the reductase-encoding gene;
wherein the fish expresses the foreign reductase-encoding gene and the reporter gene in the gonad thereof, and wherein infertility of the male of the GM fish is induced and/or the probability of infertility thereof is increased as compared to that of a wild-type counterpart if the male is treated with a reductase-activated cytotoxic prodrug.

Further in another aspect, the invention relates to a method of generating an infertile GM fish with a phenotype and/or genotype of interest comprising the steps of:
  (a) providing a homozygous male of a transgenic fish with a phenotype and/or genotype of interest;
  (b) providing a homozygous female of the aforementioned GM fish with an ovary-specific promoter;
  (c) causing the GM fish from step (b) to mate with the transgenic fish with the phenotype and/or genotype of interest from step (a) to produce a progeny;
  (d) selecting the progeny that is a female and expresses the reporter gene in the gonad; and (e) treating the selected female progeny with a therapeutically effective amount of a reductase-activated cytotoxic prodrug and thereby generating an infertile GM fish with the phenotype and/or genotype of interest.

Further in another aspect, the invention relates to a method of inducing infertility and/or causing an increased probability of infertility in a GM fish, comprising the steps of:
(a) generating the aforementioned GM fish; and
(b) treating the GM fish with a therapeutically effective amount of a reductase-activated cytotoxic prodrug and thereby generating an infertile GM fish.

Yet in another aspect, the invention relates to a method of inducing infertility and/or causing an increased probability of infertility in a GM fish with a phenotype and/or genotype of interest, comprising the steps of:
(a) providing a homozygous female of a transgenic fish with a phenotype and/or genotype of interest;
(b) providing a homozygous male of the aforementioned GM fish with three copies of the fusion transgene;
(c) causing the male GM fish from step (b) to mate with the female transgenic fish with the phenotype and/or genotype of interest from step (a) to produce a progeny;
(d) selecting the progeny that is a male and expresses the reporter gene in the gonad; and
(e) treating the selected male progeny with a therapeutically effective amount of a reductase-activated cytotoxic prodrug, and thereby generating an infertile GM fish with the phenotype and/or genotype of interest.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

C represents female Tg(ZP:NTR-EGFP). M represents Mtz-treated 6-week-old female Tg(ZP:NTR-EGFP).

Figure 5:
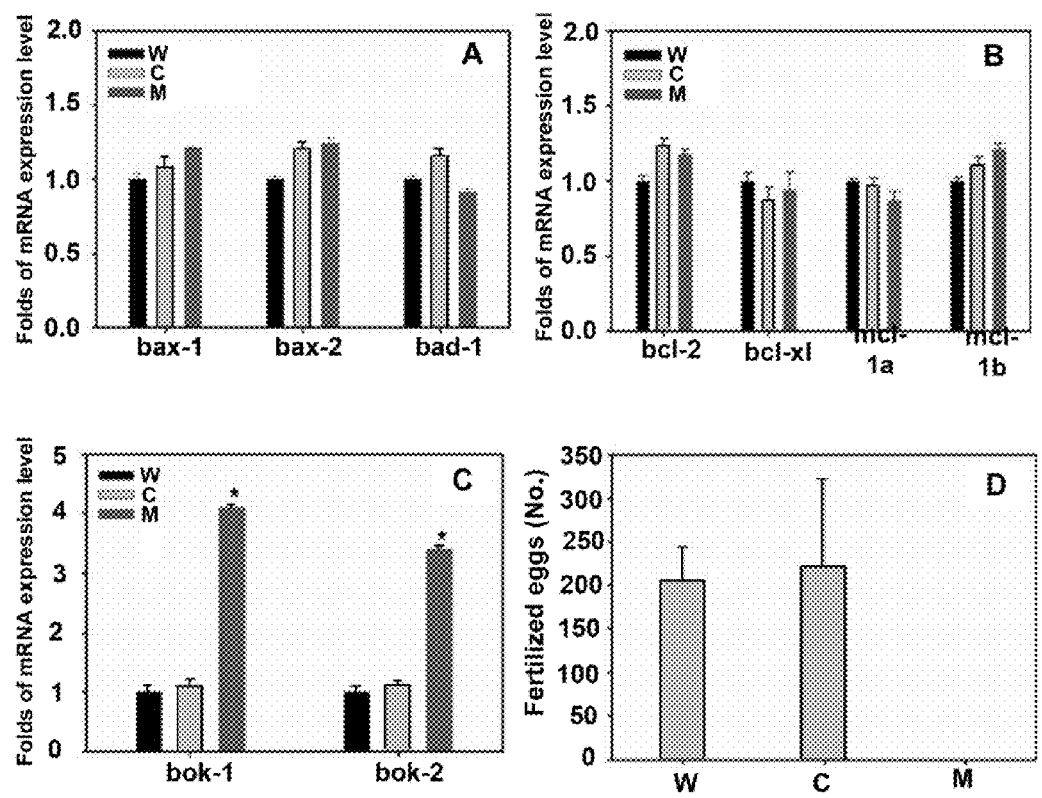
FIG. 5A is a graph showing the expression of the ovarian killer gene proapoptotic genes of the Bcl-2 gene family as detected by real-time PCR. W represents AB strain zebrafish.

FIG. 5B is a graph showing the expression of the ovarian killer gene antiapoptotic genes of the Bcl-2 gene family as detected by real-time PCR. W represents AB strain zebrafish. C represents female Tg(ZP:NTR-EGFP). M represents Mtz-treated 6-week-old female Tg(ZP:NTR-EGFP).

FIG. 5C is a graph showing that the ovarian killer genes bok-1 and bok-2 are upregulated by the NTR/Mtz oocyte-specific mediated system. The star symbols indicate significant differences ($P<0.05$). W represents AB strain zebrafish. C represents female Tg(ZP:NTR-EGFP). M represents female Tg(ZP:NTR-EGFP) with Mtz treatment.

FIG. 5D is a graph shows that Tg(ZP:NTR-EGFP) fish lose their spawning activity, which leads to infertility by oocyte-specific NTR-mediated catalysis of Mtz. The number of fertilized eggs is shown as the mean±S.D (n=20). The offspring from the AB strain zebrafish intercrossed or the female Tg(ZP:NTR-EGFP) crossed with the male AB strain zebrafish were used as controls. W represents AB strain zebrafish. C represents female Tg(ZP:NTR-EGFP). M represents female Tg(ZP:NTR-EGFP) with Mtz treatment.

Figure 6:
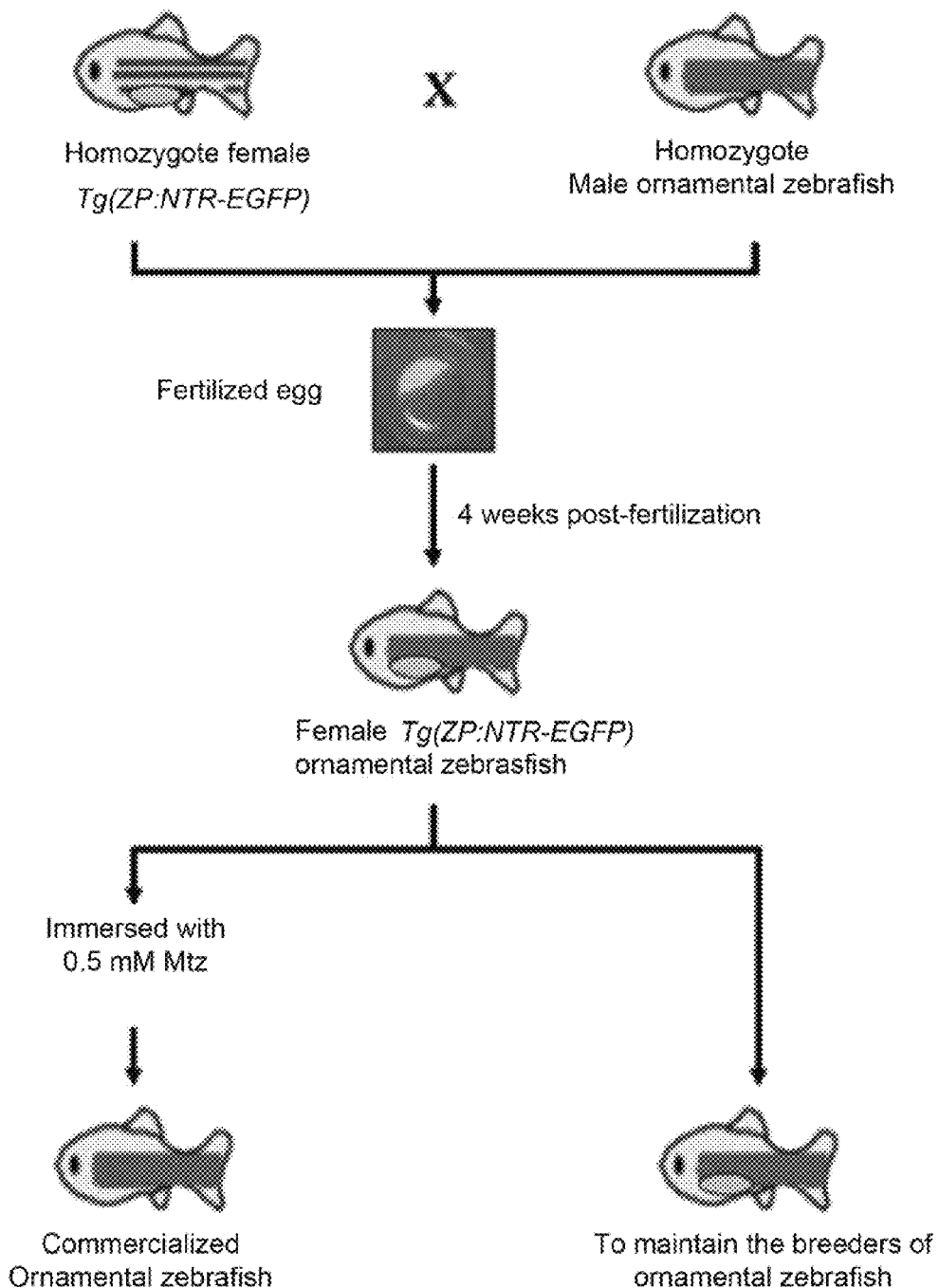

FIG. 6 is a diagram illustrating the platform technology for infertility control in genetically modified zebrafish. This example illustrates an inducible platform for infertility control practiced in transgenic ornamental zebrafish.

Figure 7A:
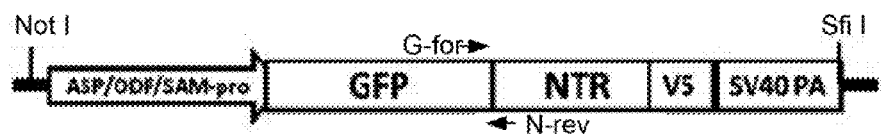

FIG. 7A is a schematic representation of a transgenic construct (Asp/Odf/Sam-eGFP:Ntr) of the engineering of transgene eGFP:Ntr, which is fused into the zebrafish genome. The Not I/Sfi I fragment consists of the zebrafish Asp/Odf/Sam gene~2-kb promoter (Asp/Odf/Sam-pro), transgene eGFP:Ntr, and the SV40 poly (A) signal (SV40 PA). The G-for/N rev primer set is used in Q-PCR to detect the eGFP:Ntr mRNA.

Figure 7B:
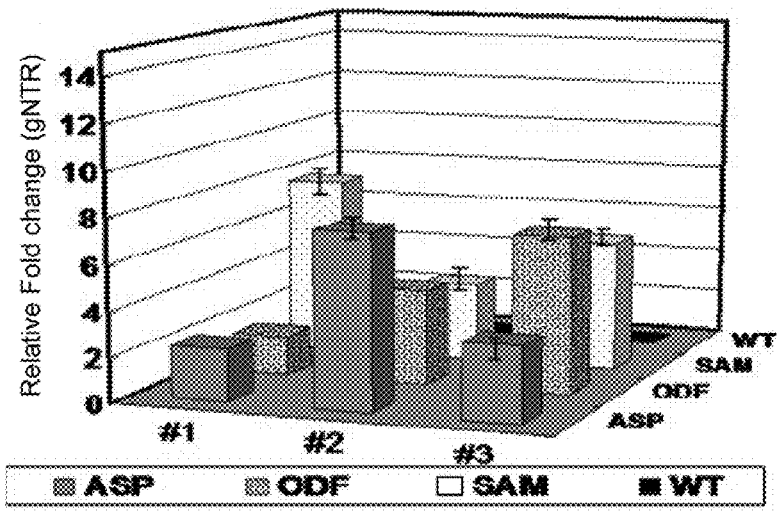

FIG. 7B is a graph display of relative quantification of eGFP:Ntr mRNA expression normalized against endogenous beta-actin mRNA using real-time reverse transcriptase polymerase chain reaction analysis. Asp/Odf/Sam#1-3 represents three independent transgenic lines generated from each transgenic construct. Control represents wild-type (WT) fish that show no discernable expression of eGFP:Ntr mRNAs.

Figure 7C:
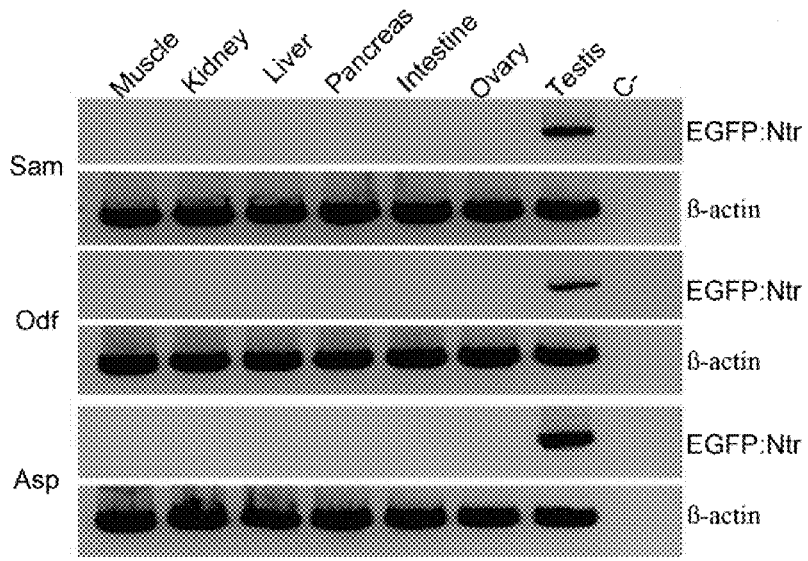

FIG. 7C is a photograph of an electrophoresis gel showing comparison of the developmental and tissue-specific expression of the endogenous Asp, Odf, and Sam genes in wild-type zebrafish and the eGFP:Ntr transgene in Tg(Asp-eGFP:Ntr) #2, Tg(Odf-eGFP:Ntr)#3, and Tg(Sam-eGFP:Ntr)#1 lines. RT-PCR was performed to detect message of endogenous Asp, Odf, and Sam genes and the eGFP:Ntr transgene. PCR products from transcripts of eGFP:Ntr and Asp, Odf, and Sam genes were detected in different adult tissues at 4 months of age. The PCR product from transcripts of β-actin was used as a control and was amplified in the same PCR reaction. C− indicates the negative water control.

Figure 8A:
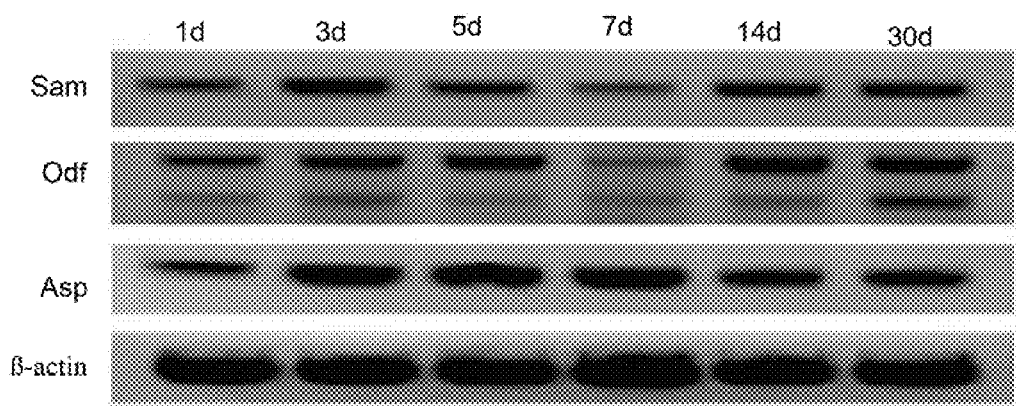

FIG. 8A is a photograph of gel electrophoresis analysis of RT-PCR products showing the expression of Asp, Odf, and Sam at various developmental stages.

Figure 8B:
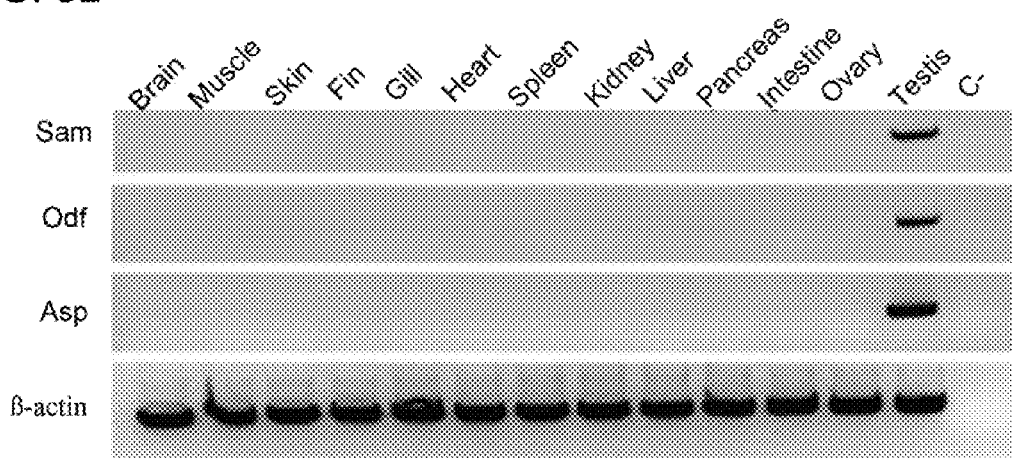

FIG. 8B is a photograph of gel electrophoresis analysis of RT-PCR products showing the expression of Asp, Odf, and Sam in adult tissues. C− negative control using water as template. PCR amplified fragments from Asp, Odf, and Sam, and β-actin cDNA, respectively. β-actin was used as a reference gene to control the amount of RNA input and sensitivity of RT-PCR analysis.

FIG. 9A is a photograph of a wholemount in situ hybridized embryo hybridized with Asp antisense riboprobe at the developmental stage of 21 dpf showing a temporal and spatial expression pattern of Asp gene.

FIG. 9B is a photograph of a whole mount in situ hybridized embryo hybridized with Odf antisense riboprobe at the developmental stage of 21 dpf showing a temporal and spatial expression pattern of Odf gene.

FIG. 9C is a photograph of a wholemount in situ hybridized embryo hybridized with Sam antisense riboprobe at the developmental stage of 21 dpf showing a temporal and spatial expression pattern of Sam gene. In situ hybridization analysis showed that those genes only expressed in the undifferentiated testis-like tissue in the juvenile stages of 21 dpf (arrow).

FIG. 9D is a photograph of a control wild type embryo hybridized with Asp sense probe.

FIG. 10A showing expression of green fluorescent protein (GFP) in the testes of transgenic eGFP:Ntr male zebrafish. a GFP-expressing testis-like gonad (arrowhead) is seen through the body wall of 28 days postfertilization (dpf) of a Tg(Asp-eGFP:Ntr) male fish.

FIG. 10 B is a photograph showing that GFP expressing testis-like gonad (arrowhead) is seen through the body wall of a 21-dpf of Tg(Odf-eGFP:Ntr) male fish.

FIG. 10C is a photograph of a bright field image showing GFP-expressing testis-like gonad (dot line) of a 36-dpf of Tg(Sam-eGFP:Ntr) male fish.

Figure 11A:
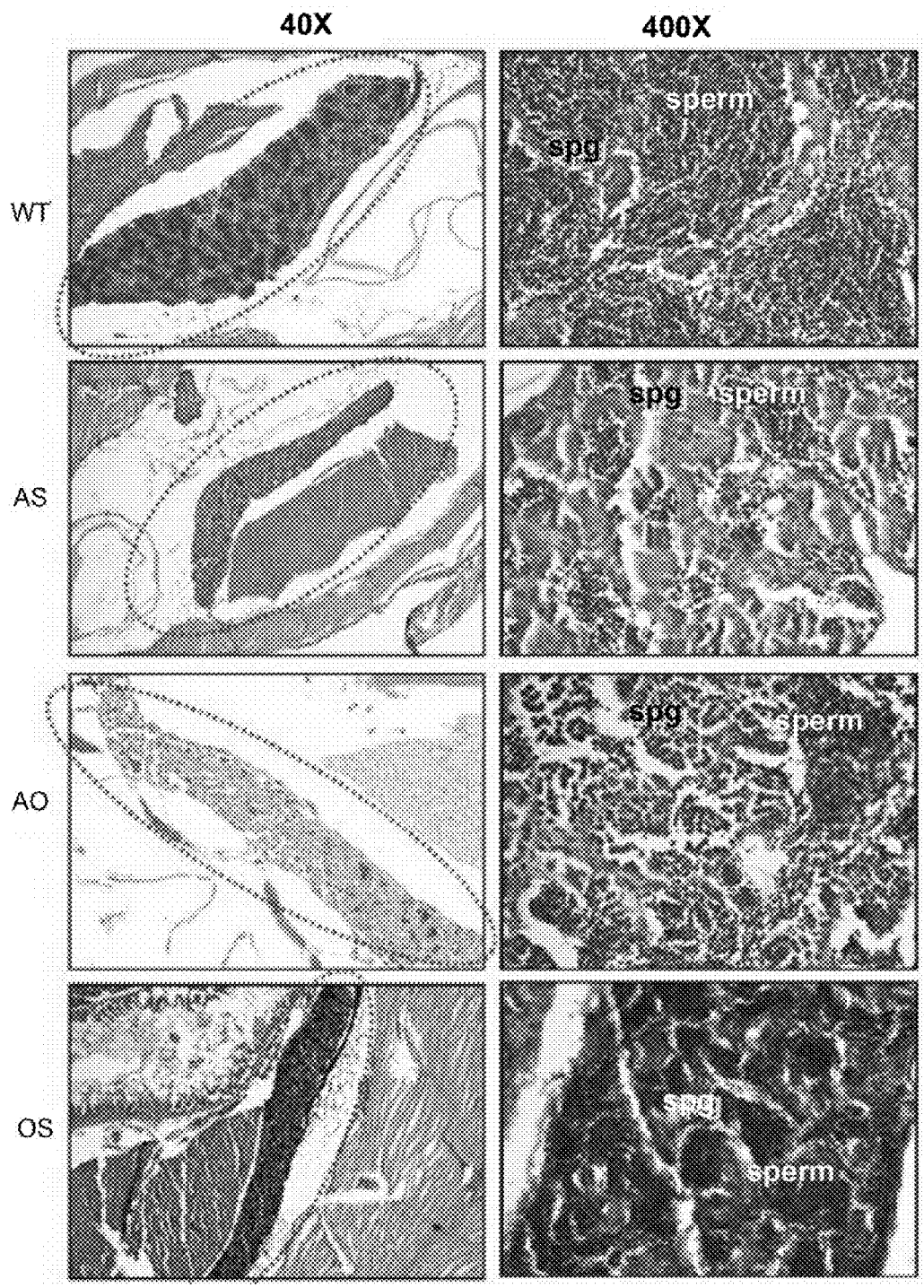

FIG. 11A is a photomicrograph showing histology of the testes from compound transgenic zebrafish lines Tg(AO-eGFP:Ntr), Tg(AS-eGFP:Ntr), and Tg(OS-eGFP:Ntr) and wild-type fish at 4 months of age. AO represents Tg(AO-eGFP:Ntr). AS represents Tg(AS-eGFP:Ntr). OS represents Tg(OS-eGFP:Ntr). AOS represents Tg(AOS-eGFP:Ntr). WT represents wild type.

FIG. 11B is a photomicrograph showing histological section of testis of 6 months old Tg(AOS-eGFP:Ntr) and wild-type fish after Met treatment. sperm spermatozoa, spg spermatogonia at different mitotic divisions. The selected region in the boxed region of insert is depicted at higher power in FIG. 11B.

FIG. 11C is a photomicrograph showing Tg(AOS-eGFP: Ntr) males lacked functional testes but showed male-pattern reproductive behavior, inducing the spawning act and competing with WT males to disrupt fertilization.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, a "prodrug" is a pharmacological substance (drug) that is administered in an inactive (or significantly less active) form. Once administered, the prodrug is metabolized in vivo into an active metabolite.

As used herein, a "reductase" is an enzyme that lowers the activation energy for a reduction reaction. Examples of reductase includes but not limited to 5-alpha reductase, Dihydrofolate reductase, HMG-CoA reductase, Methemoglobin reductase, Ribonucleotide reductase, Thioredoxin reductase, *E. coli* nitroreductase and Methylenetetrahydrofolate reductase.

As used herein, a "reporter gene" (often simply reporter) is a gene that is used to attach to another gene of interest in cell culture, animals or plants. Commonly used reporter genes that induce visually identifiable characteristics usually involve fluorescent and luminescent proteins. Examples include but not limited to the gene that encodes jellyfish green fluorescent protein (GFP), which causes cells that express it to glow green under blue light, the enzyme luciferase, which catalyzes a reaction with luciferin to produce light, and the red fluorescent protein from the gene dsRed. Another common reporter in bacteria is the GUS (UidA) gene, which encodes the protein beta-glucuronidase. This enzyme causes bacteria expressing the gene to appear blue when grown on a medium that contains the substrate analog X-gal.

The terms "testis-specific promoter" and "spermatocyte-specific promoter" are interchangeable.

The term "photosensitizer" or "photosensitizing agent" shall generally mean a substance when absorbed by cells and exposed to light, the substance becomes active and kills the cells.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

In one aspect, the invention relates to a GM fish whose genome comprises:
 (a) a fish gonad-specific promoter; and
 (b) a foreign transgene operably linked to the fish gonad-specific promoter, in which the foreign transgene comprises a suicide gene selected from the group consisting of a reductase and a photosensitizer;
wherein the reductase is operably linked to a reporter gene; and further wherein the fish gonad-specific promoter is selected from the group consisting of a fish ovary-specific promoter and a fish testis-specific promoter; and wherein a female of the fish expresses the transgene that is operably linked to the ovary-specific promoter in the ovary of the fish, and a male of the fish expresses the transgene that is operably linked to the testis-specific promoter; and further wherein infertility of the GM fish is induced and/or the probability of infertility of the GM fish is increased as compared to that of a wild-type counterpart if the GM fish expressing the reductase is treated with an effective amount of a reductase-activated cytotoxic prodrug, or if the GM fish expressing the photosensitizer is treated with light irradiation.

In one embodiment of the invention, the GM fish comprises the zp2 or zp3 promoter that is operably linked to the photosensitizer KillerRed.

In another embodiment of the invention, the GM fish comprises the Asp, Odf and/or Sam promoters operably linked to the photosensitizer KillerRed.

Further in another embodiment of the invention, the GM fish expressing the photosensitizer is a female that has been treated with light irradiation.

In another aspect, the invention relates to a genetically modified (GM) fish whose genome comprises a fusion transgene operably linked to a fish gonad-specific promoter, wherein the fusion transgene comprises:
 (a) a foreign reductase-encoding gene; and
 (b) a reporter gene operably linked to the reductase-encoding gene;
wherein the fish gonad-specific promoter is selected from the group consisting of a fish ovary-specific promoter and a fish testis-specific promoter; and wherein a female of the fish expresses the fusion transgene that is operably linked to the ovary-specific promoter in the ovary of the fish, and a male of the fish expresses the fusion transgene that is operably linked to the testis-specific promoter, and further wherein infertility of the GM fish is induced and/or the probability of infertility of the GM fish increases as compared to that of a wild-type counterpart if the GM fish expressing the fusion transgene is treated with an effective amount of a reductase-activated cytotoxic prodrug.

In another aspect, the invention relates to a progeny of the aforementioned GM fish, in which the progeny exhibits the expression of the transgene in the gonad thereof.

In one embodiment of the invention, the invention relates to a progeny of a homozygous female of the aforementioned GM fish, in which the progeny exhibits the expression of transgene in the gonad thereof.

The reductase-activated cytotoxic prodrug may be selected from the group consisting of metronidazole (Mtz) and 5-(aziridin-1-yl)-2,4-dinitrobenzamide.

In one embodiment of the invention, the reductase-encoding gene of the fusion transgene in the GM fish encodes nitroreductase (NTR). The fish expressing the fusion transgene reductase exhibits gonadal dysgenesis if treated with an effective amount of a reductase-activated cytotoxic prodrug.

In another embodiment of the invention, the GM fish expressing the fusion transgene is a female that has been treated with the prodrug and exhibits infertility.

The fish gonad-specific promoter may be selected from the group consisting of a fish ovary-specific promoter and a fish testis-specific promoter.

In one embodiment of the invention, the fish gonad-specific promoter operably linked to the fusion transgene of the GM fish is a fish ovary-specific promoter.

In another aspect, the invention relates to a GM fish progeny, whose maternal parent is a homozygous female of the aforementioned GM fish with a fish ovary-specific promoter operably linked to the fusion transgene, and paternal parent a homozygous male transgenic fish with a phenotype and/or genotype of interest, wherein the GM fish progeny exhibits the expression of the fusion transgene or photosensitizer in the gonad thereof and manifests the phenotype and/or genotype of interest.

In one embodiment of the invention, the aforementioned GM fish progeny is infertile.

In another embodiment of the invention, the aforementioned GM fish progeny exhibits a phenotype of interest by manifesting an exogenous fluorescent protein.

The ovary-specific promoter operably linked to the aforementioned transgene may be selected from the group consisting of zp2 (SEQ ID NO: 44) and zp3 promoter (SEQ ID NO: 44). The aforementioned GM fish exhibits infertility if the fish is a female that expresses the reductase and has been treated with a therapeutically effective amount of a reductase-activated cytotoxic prodrug.

Alternatively, the aforementioned GM fish exhibits infertility if the fish is a female that expresses the photosensitizer and has been treated with light irradiation.

In another embodiment of the invention, the fish gonad-specific promoter operably linked to the fusion transgene of the GM fish is a fish testis-specific promoter. The testis-specific promoter may be selected from the group consisting of Asp, Odf and Sam promoters.

Further in another embodiment of the invention, the aforementioned GM fish with a fish testis-specific promoter exhibits an increased probability of infertility as compared to that of a wild-type counterpart if the fish is a male that expresses reductase has been treated with a therapeutically effective amount of a reductase-activated cytotoxic prodrug.

In another embodiment of the invention, the aforementioned GM fish with a fish testis-specific promoter exhibits an increased probability of infertility as compared to that of a wild-type counterpart if the fish is a male that expresses photosensitizer has been treated with light irradiation.

Further in another aspect, the invention relates to a GM fish progeny of a homozygous male and homozygous female of the aforementioned GM fish with a fish testis-specific promoter operably linked to the fusion transgene reductase, in which the homozygous male of the aforementioned GM fish exhibits an increased probability of infertility as compared to that of a wild-type counterpart if treated with a therapeutically effective amount of a reductase-activated cytotoxic prodrug.

Alternatively, the invention relates to a GM fish progeny of a homozygous male and homozygous female of the aforementioned GM fish with a fish testis-specific promoter operably linked to the foreign transgene photosensitizer, in which the homozygous male of the aforementioned GM fish exhibits an increased probability of infertility as compared to that of a wild-type counterpart if treated with light irradiation.

In one embodiment of the invention, the GM fish progeny as mentioned immediately above comprises at least 2 copies of the fusion or foreign transgene with each copy operably linked to a different testis-specific promoter. For example, such a GM fish progeny may be selected from the group consisting of
(a) a double transgenic: Tg(AO-EGFP:Ntr)[Tg(Asp-EGFP:Ntr);Tg(Odf-EGFP:Ntr)], Tg(AS-EGFP:Ntr)[Tg(Asp-EGFP:Ntr);Tg(Sam-EGFP:Ntr)], and Tg(OS-EGFP:Ntr)[Tg(Odf-EGFP:Ntr);Tg(Sam-EGFP:Ntr)]; and
(b) a triple-transgenic: Tg(AOS-EGFP:Ntr)[Tg(Asp-EGFP:Ntr; Odf-EGFP:Ntr; Sam-EGFP:Ntr).

Alternatively, such a GM fish progeny may be selected from the group consisting of:
(a) a double transgenic: Tg(AO-KillerRed)[Tg(Asp-KillerRed);Tg(Odf-KillerRed)], Tg(AS-KillerRed)[Tg(Asp-KillerRed);Tg(Sam-KillerRed)], and Tg(OS-KillerRed)[Tg(Odf-KillerRed);Tg(Sam-KillerRed)]; and
(b) a triple-transgenic: Tg(AOS-KillerRed)[Tg(Asp-KillerRed; Odf-KillerRed; Sam-KillerRed).

Further in another aspect, the invention relates to a GM fish whose genome comprises at least two copies of a fusion transgene with each copy operably linked to a different fish testis-specific promoter, wherein the fusion transgene comprises:
(a) a foreign reductase-encoding gene; and
(b) a reporter gene operably linked to the reductase-encoding gene;
wherein the fish expresses the foreign reductase-encoding gene and the reporter gene in the gonad thereof, and wherein infertility of a male of the GM fish is induced and/or the probability of infertility thereof increases as compared to that of a wild-type counterpart if the male is treated with a reductase-activated cytotoxic prodrug.

In one embodiment of the invention, the aforementioned GM fish has three copies of the fusion transgene.

Further in another aspect, the invention relates to a method of generating an infertile GM fish with a phenotype and/or genotype of interest comprising the steps of:
(a) providing a homozygous male of a transgenic fish with a phenotype and/or genotype of interest;
(b) providing a homozygous female of the aforementioned GM fish with an ovary-specific promoter;
(c) causing the GM fish from step (b) to mate with the transgenic fish with the phenotype and/or genotype of interest from step (a) to produce a progeny;
(d) selecting the progeny that is a female and expresses the reporter gene in the gonad; and
(e) treating the selected female progeny with a therapeutically effective amount of a reductase-activated cytotoxic prodrug and thereby generating an infertile GM fish with the phenotype and/or genotype of interest.

Alternatively, the invention relates to a method of generating an infertile GM fish with a phenotype and/or genotype of interest comprising the steps of:
(a) providing a homozygous male of a transgenic fish with a phenotype and/or genotype of interest;
(b) providing a homozygous female of a GM fish expressing a photosensitizer operably linked to an ovary-specific promoter;
(c) causing the GM fish from step (b) to mate with the transgenic fish with the phenotype and/or genotype of interest from step (a) to produce a progeny;
(d) selecting the progeny that is a female and expresses the photosensitizer in the gonad; and
(e) treating the selected female progeny with light irradiation and thereby generating an infertile GM fish with the phenotype and/or genotype of interest.

In one embodiment of the invention, the phenotype of interest is a manifestation of an exogenous fluorescent protein.

Further in another aspect, the invention relates to a method of inducing infertility and/or causing an increased probability of infertility in a GM fish, comprising the steps of:
(a) generating a GM fish expressing reductase; and
(b) treating the GM fish with a therapeutically effective amount of a reductase-activated cytotoxic prodrug and thereby generating an infertile GM fish.

Yet in another aspect, the invention relates to a method of inducing infertility and/or causing an increased probability of infertility in a GM fish with a phenotype and/or genotype of interest, comprising the steps of:
(a) providing a homozygous female of a transgenic fish with a phenotype and/or genotype of interest;
(b) providing a homozygous male of the aforementioned GM fish with three copies of the fusion transgene;
(c) causing the male GM fish from step (b) to mate with the female transgenic fish with the phenotype and/or genotype of interest from step (a) to produce a progeny;
(d) selecting the progeny that is a male and expresses the reporter gene in the gonad; and
(e) treating the selected male progeny with a therapeutically effective amount of a reductase-activated cytotoxic prodrug, and thereby generating an infertile GM fish with the phenotype and/or genotype of interest.

Alternatively, step (b) above may provide a homozygous male of a GM fish with three copies of the foreign transgene photosensitizer, step (d) above provides selecting the progeny that is a male and expresses the photosensitizer in the gonad, and step (e) above provides treating the selected male progeny with light irradiation.

Induction of Female Infertility in Genetically Modified Fish
I. The Suicide Gene Nitroreductase
Materials and Methods
Zebrafish Line and Maintenance AB strain zebrafish were purchased from the zebrafish international resource center. The fish were raised and maintained in a freshwater recirculating tank with a controlled light cycle of 14 h light/10 h dark at 28° C. The intercrossed progeny from the AB strain zebrafish were used for microinjection. The age of the juveniles is indicated as the days posthatching.

Construction of Transgenic Constructs

The T2KXIGΔIN vector backbone, including the expression cassette (ef1α promoter, egfp gene (SEQ ID NO: 45), SV 40 polyadenylation) and flanks to the expression cassette of Tol2 transposon arms (500 bp left arm and 500 bp right arm), was kindly provided by Dr. Kawakami (Kawakami K (2004) "Transgenesis and gene trap methods in zebrafish by using the Tol2 transposable element" *Methods Cell Biol* 77:201-222, which is herein incorporated by reference in its entirety). The nitroreductase (ntr) gene (SEQ ID NO: 46) was cloned directly from *Escherichia coli* BL21 genomic DNA by PCR using the forward primer ntr(f) 5' ACTACCGGTATGGATATCATTTCTGTCGCCTTA-3' (SEQ ID NO: 1) and the reverse primer ntr(r) 5'-ACTACCGGTGTCACTTCGGTTAAGGTGATGTTTTG-3' (SEQ ID NO: 2). The primer design enabled the creation of an AgeI restriction site. The ntr gene PCR product (~671 bp) was digested with AgeI and cloned into the T2KXIGΔIN vector, downstream of the ef1α promoter to generate the vector pT2-EF1α-NTR-EGFP. The 2.2 kb 5' flanking region of the zona pellucida (zp3) gene, which is capable of driving oocyte-specific expression, was amplified by PCR from zebrafish genomic DNA using the forward primer zp3(f) 5'-AGTGGGCCCAATAAATGTCTGAAACCTTATCTTTGGCTTTT (SEQ ID NO: 3) and the reverse primer zp3(r) 5'-ACTACCGGTCCTTGAAGACTCAATGCCACAATGCTCATC (SEQ ID NO: 4). The forward and reverse primer designs enabled creation of XhoI and SalI restriction sites, respectively. The zp3 promoter (SEQ ID NO: 43) PCR product was digested with XhoI and SalI and cloned into a pT2-EF1α-NTR-EGFP vector to replace the ef1α promoter, thereby generating the expression construct pT2-ZP-NTR-EGFP. For genomic integration and generation of the stable transgenic line Tg(ZP:NTR-EGFP), this construct was comicroinjected with Tol2 transposon mRNA into single-cell stage embryos.

Defection of Genomic Integration and NTR-EGFP Expression

In order to screen the $F_0$ transgenic founders, the $F_1$ offspring from each injected fish were used for the detection of germ line transmission and expression of ntr-egfp. The embryos were dissolved in 1.2 ml of extraction buffer (0.5% SDS; 100 mM NaCl; 10 mM Tris-Cl; pH 8.0; 25 mM EDTA, pH 8.0; 0.1 mg/ml proteinase K) at 55° C. overnight and centrifuged at 12,000 rpm for 1 min. An equal volume of a saturated phenol solution was added to the supernatant and mixed gently by inversion. After centrifugation at 12,000 rpm for 10 min, the upper layer of the solution was carefully transferred to clean microcentrifuge tubes. The above steps of phenol extraction were repeated several times, and then the phenol was replaced with phenol-chloroform (1:1) solution the final time and centrifuged again to collect the supernatants in clean microcentrifuge tubes. The same volume of 100% ethanol and 5 µl of 3M sodium acetate were added, and the tubes were stored at −20° C. for 20 min. The genomic DNA pellet was collected and air-dried for 10 min after centrifugation at 12,000 rpm for 10 minutes. The pellet was dissolved in TE buffer and used as template for the identification of genomic integration by PCR. The $F_1$ embryos were collected for the extraction of total RNA using TRIzol reagent (Invitrogen, USA). First-strand cDNA was synthesized in a 20 µl RT reaction from 1 µl of total RNA using the SuperScript III First-Strand kit (Invitrogen). The PCR was performed from genomic DNA and cDNA using the forward primer ntr-id (f) 5'-ATGGATATCATTTCTGTCGCCTTA (SEQ ID NO: 5) and the reverse primer egfp (r) 5'-TTACTTGTACAGCTCGTCCATGCCGAG (SEQ ID NO: 6), respectively, to detect the genomic integration and expression of ntr-egfp.

Mtz Preparation and Treatment

Metronidazole (Mtz) [1-(2-hydroxyethyl)-2-methyl-nitroimidazole] (Sigma M3761) was dissolved in standard zebrafish embryo medium containing 0.1% DMSO with vigorous shaking and was placed in a dark place to prevent photoinactivation of Mtz. The intercrossed $F_2$ progeny from the $F_1$ Tg(ZP:NTR-EGFP) were collected and incubated at 28° C. in an aquarium. The $F_2$ female Tg(ZP:NTR-EGFP) with NTR-EGFP expression were screened at 28 days posthatching under fluorescent microscopy and incubated in a dark tank with embryo medium containing 0.1% DMSO and 5 mM Mtz (n=20/per tank; duplicate). The female Tg(ZP:NTR-EGFP) incubated in embryo medium with 0.1% DMSO were used as the control (n=20/per tank; duplicate). The embryo medium with 0.1% DMSO and 5 mM Mtz was renewed every week to maintain medium quality and sufficient Mtz substrate. The adult Tg(ZP:NTR-EGFP) with Mtz treatment were used to observe oocyte development by histological analyses and to evaluate the reproductive capacity.

Histological Analysis and Evaluation of Reproductive Capacity

Ovary tissues were harvested from adult zebrafish and fixed overnight in PBS buffer containing 4% paraformaldehyde (PFA) at 4° C. The samples were dehydrated in methanol and embedded in agarose. The samples were sectioned at 8 µm and then mounted on poly-L-lysine coated slides. The histological analysis was carried out by hematoxylin-eosin (H&E) staining using standard protocols. To evaluate the reproductive capacity of female Tg(ZP:NTR-EGFP) with Mtz treatment, the fertilized egg of a female Tg(ZP:NTR-EGFP) crossed with a male AB strain wild-type zebrafish was used as a reference.

Detection of Bcl-2 Gene Family by Real-Time Quantitative PCR

Total RNAs from ovary tissues of 3-month-old AB strain wild type, transgenic line Tg(ZP:NTR-EGFP), and Mtz-treated 6-week-old Tg(ZP:NTR-EGFP) transgenic zebrafish were extracted respectively using TRIZOL (Invitrogen). For real-time quantitative PCR, first-strand cDNAs were synthesized by High Capacity cDNA Reverse Transcription Kit (Applied Biosystems) with random primers. Quantitative PCR was performed by using Power SYBR Green PCR Master Mix in LightCycler 480 System (Roche). Gene-specific primers of Bcl-2 gene family were designed by Roche ProbeFinder software for real-time quantitative PCR. The transcript of ef-1α gene was used as an endogenous control. Primer sets used in quantitative PCR are listed as follows: bcl-2 forward, 5'-tggcgtcccaggtagataa t-3' (SEQ ID NO: 7) and reverse, 5'-accgtacatctccac gaagg-3' (SEQ ID NO: 8); bcl-xl forward, 5'-ggcttgtttgcttggttgac (SEQ ID NO: 9) and reverse 5'-tggtg-caatggctcatacc-3'(SEQ ID NO: 10); mcl-1a forward, 5'-ggatcctcaaaaacaagagctg-3' (SEQ ID NO: 11) and reverse, 5'-catgacggacaacagactctac a-3' (SEQ ID NO: 12); mcl-1b forward, 5'-gcacgagctcgcttacaaa-3'(SEQ ID NO: 13) and reverse, 5'-ctctgttgccacttgcttga-3' (SEQ ID NO: 14); bax-1 forward, 5'-gcccgtgagatcttctctga-3' (SEQ ID NO: 15) and reverse, 5'-tcaggaaccctggttgaaat-3' (SEQ ID NO: 16); bax-2 forward, 5'-gttcacagatggccagatca-3' (SEQ ID NO: 17) and reverse, 5'-tctgaaacaattctgggtaggc-3' (SEQ ID NO: 18); bad-1 forward, 5'-agatcccgctcagctcct-3' (SEQ ID NO: 19) and reverse, 5'-ttcctgcactttttactctcttca-3' (SEQ ID NO: 20); bok-1 forward, 5'-cgaaaaggtttggaaaaacataa-3' (SEQ ID NO: 21) and reverse, 5'-ccgaacacagtccacagcta-3' (SEQ ID NO: 22); bok-2 forward, 5'-gtgccatggctcaaaaaga-3' (SEQ ID NO: 23) and reverse, 5'-gagtccatgtttaccacacatttt-3' (SEQ ID NO: 24); ef-1α forward, 5'-cctctttctgttacctggcaaa-3' (SEQ ID NO: 25) and reverse, 5'-cttttcctttcccatgattga-3' (SEQ ID NO: 26).

TUNEL Cell Death Assay

The TUNEL cell death assay was performed using the In Situ Cell Death Detection Kit (Roche No. 11684817910). After the fixation of ovary tissue in 4% PFA and sectioning, the ovary sections were preincubated in PBST and then labeled with the TUNEL kit for 1 hr at 37° C. The sections were washed with PBST and visualized by microscopy.

Results and Discussion

Expression of NTR-EGFP Controlled by Zona Pellucida Promoter.

Figure 1A:
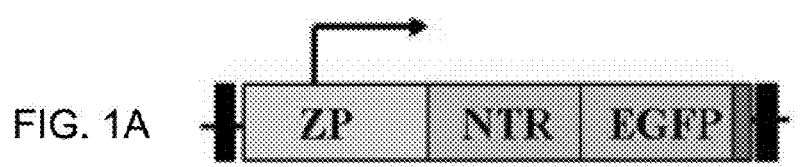
FIG. 1A is a schematic representation of a diagram illustrating the main features of the pT2-ZP-NTR-EGFP plasmid for the establishment of the Tg(ZP:NTR-EGFP) fish with oocyte specific expression of NTR-EGFP fusion protein. The expression of NTR-GFP fusion is controlled by the oocyte-specific zp promoter (the bent arrow). Two Tol2 transposon elements (black box) flank the expression cassettes. The SV 40 polyadenylation site is indicated by the gray box.

NTR-mediated cell and tissue ablation has been previously applied in zebrafish developmental and regeneration studies, and manipulation of NTR/Mtz system-mediated cell ablation has been described. In order to cause Mtz-dependent oocyte death, NTR must be specifically expressed in the oocyte. Vertebrate zona pellucida (zp) proteins, which are encoded by multiple zp gene families, are glycoprotein and extracellular matrix structures that surround the membrane of an oocyte. In zebrafish, the zp2 and zp3 genes have ovary-specific expression, and the zp3 promoter (SEQ ID NO: 43), which is oocyte-specific, has been cloned. In the present study, a 2.2 kb promoter upstream of the zp3 ATG start codon was amplified by PCR and cloned into T2KXIGΔIN to generate the plasmid pT2-ZP-NTR-EGFP for expression of the NTR-EGFP reporter protein, which enables simple observation of oocyte ablation by Mtz (Shao-Yang Hu et al., "Nitroreductase-mediated Gonadal Dysgenesis for Infertility Control of Genetically Modified Zebrafish" Mar Biotechnol DOI 10.1007/s10126-009-9244-8, which is herein incorporated by reference in its entirety). The Tg(ZP:NTR-EGFP) fish were established by Tol2 transposon-mediated DNA integration and characterized by EGFP expression analyses (FIG. 1A).

Figure 1B:
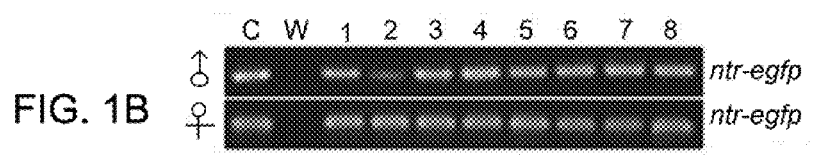
FIG. 1B is a photograph of a gel electrophoresis analysis of PCR products confirming the genomic integration and germ line transmission of the NTR-EGFP expression cassette in the F1 Tg(ZP:NTR-EGFP) inherited from the transgenic founder. C represents using pT2-NTR-EGFP as a positive control. W represents the AB strain zebrafish. Numbers 1~8 for each transgenic male and female founder.
Figure 1C:
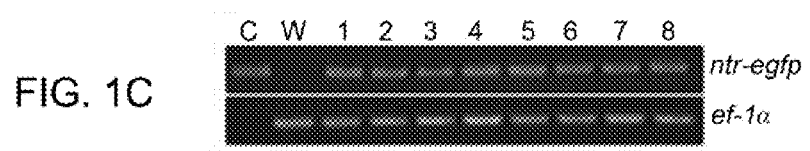
FIG. 1C is a photograph of a gel electrophoresis analysis of RT-PCR products confirming the mRNA expression of NTR-EGFP in the F1 progeny. Ef-1α was used as an internal control.
Figure 1D:
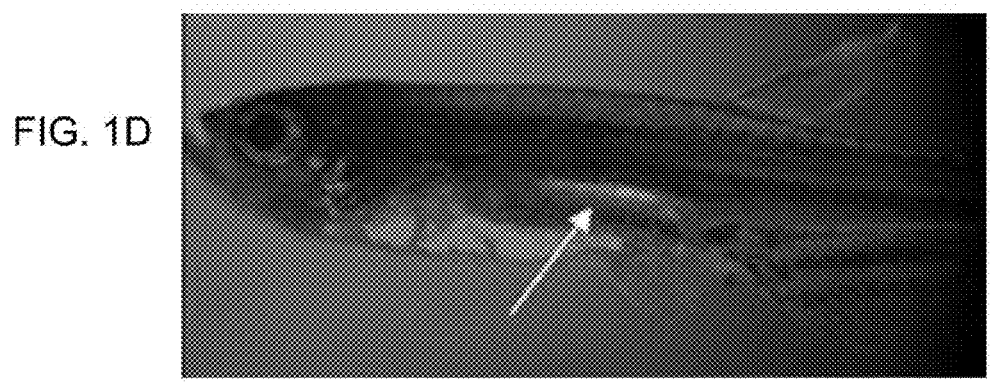
FIG. 1D is a photograph of a transgenic fish showing that the expression of the NTR-EGFP fusion protein was observed as early as 28 days posthatching in the gonads (arrow indicated) of the F1 Tg(ZP:NTR-EGFP) female fish under fluorescent microscopy.
Figure 1E:
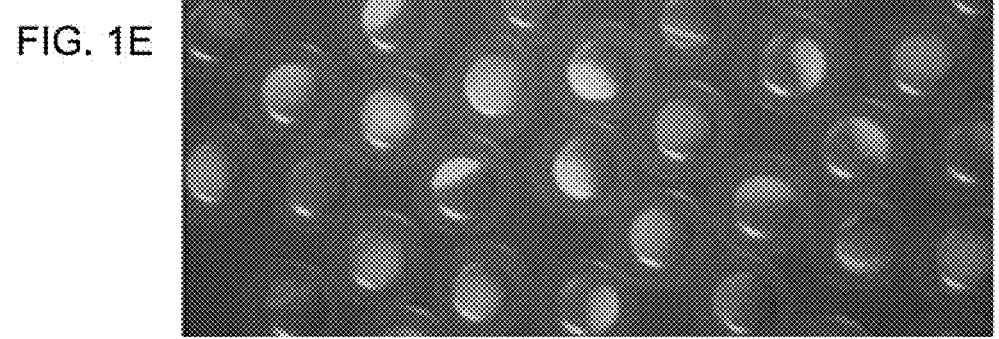
FIG. 1E is a photomicrograph of newly fertilized F2 Tg(ZP:NTR-EGFP) embryos possess maternally expressed NTR-EGFP fusion protein in the cytoplasm.

Eight female and eight male transgenic founders were screened from fifty pT2-ZP-NTR-EGFP plasmid-injected fish. Germ-line transmission of the NTR-EGFP expression cassette in each $F_1$ Tg(ZP:NTR-EGFP) was confirmed by PCR using the genomic DNA as a template (FIG. 1B). Because zona pellucida proteins only exist in female fish, mRNA expression of ntr-egfp in the $F_1$ progeny was confirmed by RT-PCR in each transgenic female founder (FIG. 1C). The $F_1$ progeny from intercrossed transgenic founders were maintained to generate the $F_2$ progeny. Similar to a previous report, which mentioned that zebrafish zp3 mRNA expression was initiated at 21 days posthatching, specific expression of EGFP in the gonads was first detectable through the body in the juvenile female $F_1$ Tg(ZP:NTR-EGFP) at 21~28 days posthatching (FIG. 1D). Certainly, the $F_2$ fertilized eggs from the intercrossed $F_1$ Tg(ZP:NTR-EGFP) fish contain maternally expressed NTR-EGFP fusion protein and are bright green when visualized by fluorescence illumination. The EGFP fluorescence triggered by the zp3 promoter during embryogenesis is strongest within the cytoplasm of the eggs (FIG. 1E) and then gradually disappears during the successive stages of somitogenesis.

Oocyte Dysgenesis Induced by Mtz in a NTR-Specific Manner

In order to determine the tolerable concentration of Mtz for zebrafish, AB strain zebrafish embryos at the single-cell stage were incubated at 28° C. in a range of Mtz concentrations (0-20 mM). We observed obvious abnormal development of larvae at 3 days postfertilization (dpf). The larvae were dead at 5 dpf after consecutive immersions in 15 nM Mtz (100%, n=26/26) and 20 mM Mtz (100%, n=30/30). The nonspecific death of the larvae was first observed at 6 dpf after consecutive immersions in 10 mM Mtz (23%, n=7/30). In contrast, we observed that no larvae died after at least 10 dpf of consecutive immersion in 5 mM Mtz (0%, n=30). Therefore, the optimal Mtz concentration used in the present experiment was 5 mM.

Figure 2:
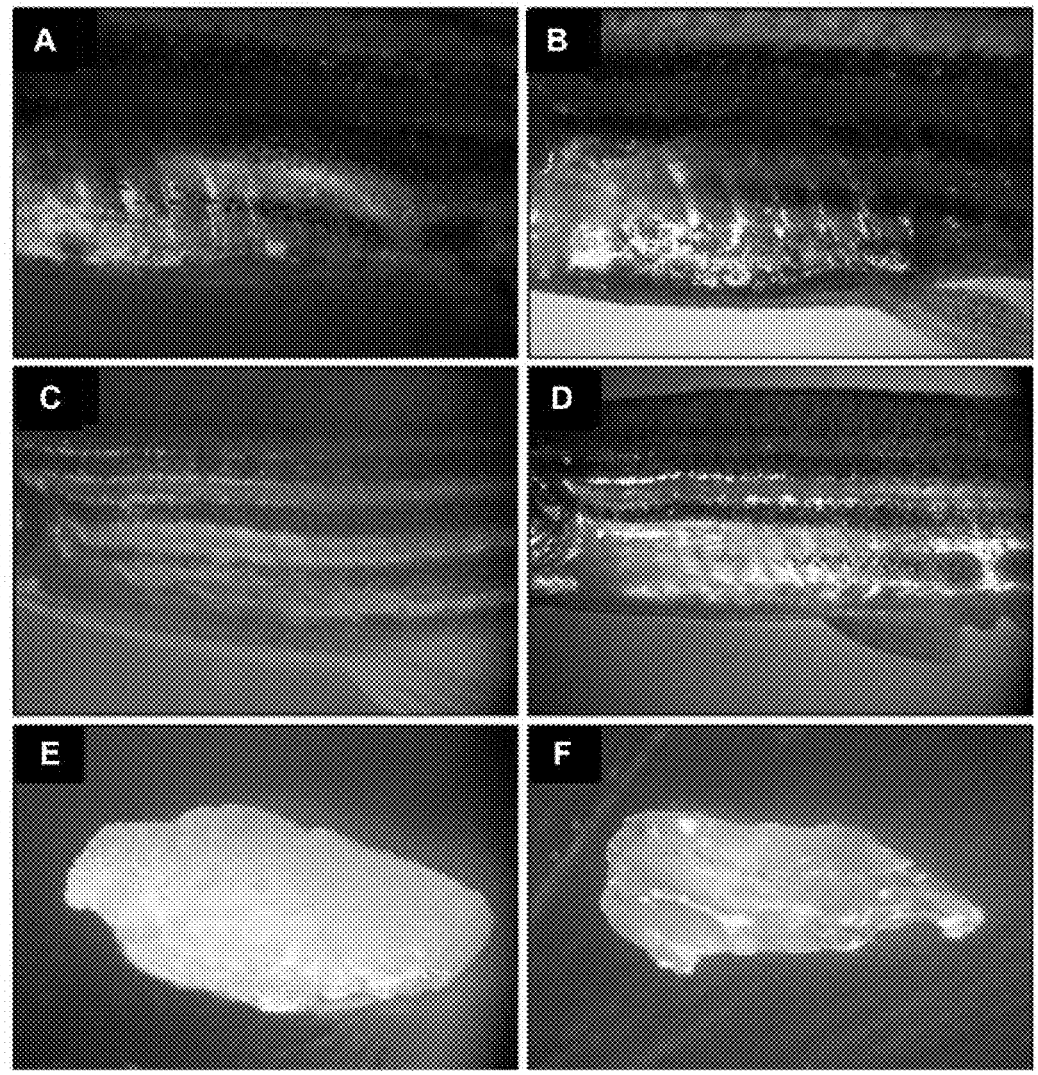
FIG. 2A is a photograph of a 6-week-old female Tg(ZP:NTR-EGFP) fish showing the oocyte-specific expression of NTR-EGFP.
FIG. 2B is a photograph of a Mtz-treated 6-week-old female Tg(ZP:NTREGFP) showing the expression of NTR-EGFP eliminated by Mtz immersion. The result indicates that oocyte dysgenesis was induced by Mtz in a NTR-dependent manner.
FIG. 2C is a photograph of an adult female Tg(ZP:NTR-EGFP) fish showing the oocyte-specific expression of NTR-EGFP.
FIG. 2D a photograph of a Mtz-treated adult female Tg(ZP:NTREGFP) showing the expression of NTR-EGFP eliminated by Mtz immersion.
FIG. 2E is a photograph of the results of an anatomical analysis showing that a complete ovary structure of an adult female Tg(ZP:NTR-EGFP) is made up of oocytes.
FIG. 2F is a photograph of an ovary of a Mtz-treated adult female Tg(ZP:NTR-EGFP) showing ovarian atrophy without oocyte formation.

To evaluate the ability of NTR to induce Mtz-susceptibility in oocytes, stable $F_2$ female Tg(ZP:NTR-EGFP) fish with gonad-specific EGFP expression were screened at 28 days post-hatching and then shifted to 5 mM Mtz cultured medium. In contrast to the female Tg(ZP:NTR-EGFP) fish without Mtz treatment, expression of EGFP in the gonads of female Tg(ZP:NTR-EGFP) fish with Mtz treatment was eliminated gradually and disappeared completely at 6 weeks posthatching (FIGS. 2A and 2B). Obviously, the elimination of EGFP expression was induced by Mtz treatment due to the specific expression of NTR in the gonads. It is well known that zp proteins are the major component of the extracellular structural coat of mature oocytes. According to a previous report, the zp genes are abundantly transcribed during oogenesis and zp mRNA accounts for 10.3% of the total transcripts expressed in the ovary. It is apparent that the expression of the NTR-EGFP fusion was strongly interspersed in the ovary of the adult female Tg(ZP:NTR-EGFP) fish (FIG. 2C). Morphological observation after continuous Mtz treatment indicated that the protuberant shape of the ovary was completely formed in the adult Tg(ZP:NTR-EGFP) female fish, whereas, a flat abdomen without EGFP expression was observed in the adult Tg(ZP:NTR-EGFP) female fish (FIGS. 2C and 2D). In order to evaluate the anatomical changes in the ovary induced by Mtz treatment, the ovarian tissue was harvested and dissected. The anatomical analysis showed that the entire Ovary was made up of sufficient oocytes and developed normally in the Tg(ZP:NTR-EGFP) female fish (FIG. 2E); however, the ovary was lacking oocytes due to atrophy and dysgenesis in the Mtz-treated fish (FIG. 2F). These results indicate that Mtz mediated oocyte dysgenesis through NTR.

Oogenesis is Blocked by NTR Catalysis of Mtz Substrate

Figure 3:
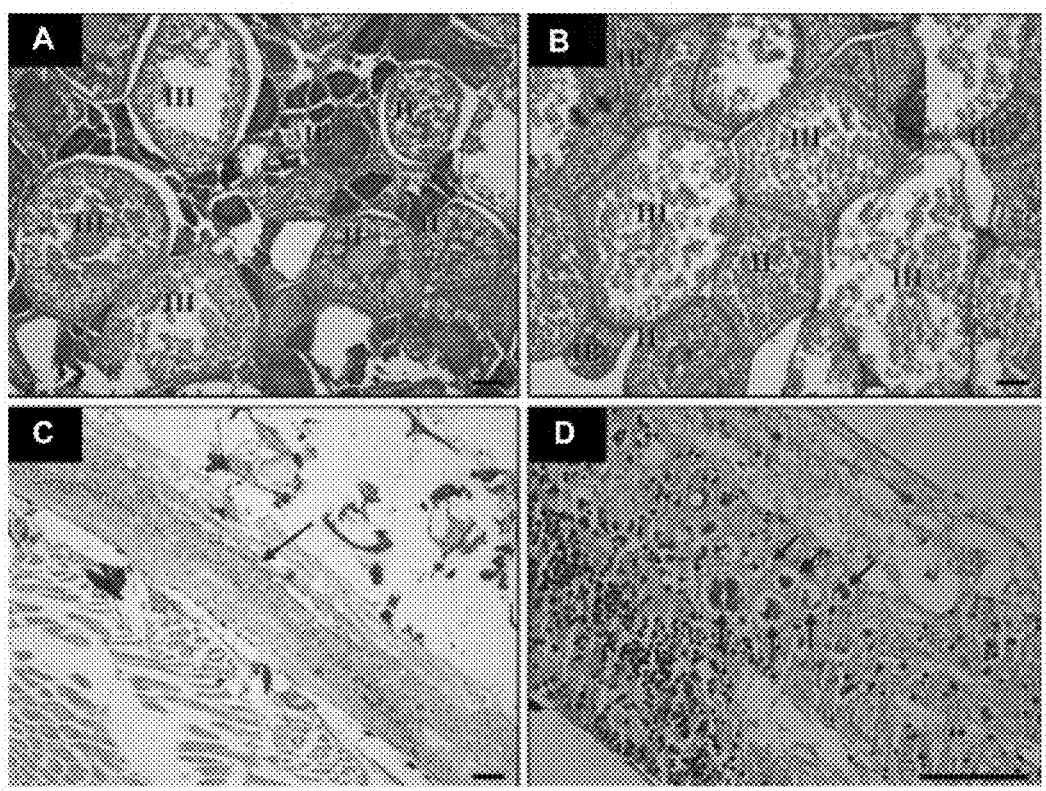
FIG. 3A is a photomicrograph showing normal development of oocytes detected in an adult female AB strain zebrafish by hematoxylin-eosin (H&E) staining. The Roman numerals indicate the stages of developing oocytes. The black bar represents 100 μm.
FIG. 3B is a photomicrograph showing normal development of oocytes detected in an adult female Tg(ZP:NTR-EGFP) zebrafish by H&E staining. The black bar represents 100 μm.
FIG. 3C is a photomicrograph showing dysgenesis of oocytes in the gonads of an adult Tg(ZP:NTR-EGFP) female fish with Mtz treatment. The effects of Mtz treatment on oocyte structure in the Tg(ZP:NTR-EGFP) was detected by H&E staining. The arrow indicates the site of the gonad. The black bar represents 100 μm.
FIG. 3D is a magnified photomicrograph of FIG. 3C showing a few of developmental oocytes being stuck at the IA stage of oogenesis. The arrows indicate that the nucleus is filled with most of the oocytes at the prefollicle primary growth stage. The black bar represents 100 μm.

To further understand the effect of Mtz treatment on oocyte maturation, the formation of oocytes was detected by H&E staining. Oogenesis in zebrafish has been described to occur in five stages according to oocyte size and certain morphologic features. In stage IA (7~20 µm), the oocyte lies within a nest and the nucleus fills most of the oocyte compared to the cytoplasm at the pre-follicle primary growth stage. In stage IB (20~140 µm), the oocyte is surrounded by the follicle at the follicle primary growth stage. In stage II (140~340 µm), there is an increasing number of yolk vesicles at the yolk vesicle stage. In stage III (340~690 µm), there is an accumulation of yolk bodies, which obscures the germinal vesicles at the vitellogenesis stage. In stage IV (690~730 µm), the oocyte initiates meiosis and becomes transparent at the oocyte maturation stage. In stage V (730~750 µm), the mature egg leaves the follicle during ovulation. Oocytes with normal development are similar between the 6-week-old AB strain and the Tg(ZP:NTR-EGFP) fish, and histological analysis showed that the main oocytes were proceeding as stage II and stage III (FIGS. 3A and 3B). In contrast, ovary development was incomplete in the Mtz-treated 6-week-old Tg(ZP:NTR-EGFP) fish due to blockade of oogenesis (FIG. 3C). The zp3 gene that encodes the zp protein is a main structure in the fish chorion and its expression accompanies the development of oocytes. Because ablation of the oocytes induced by Mtz treatment in the Tg(ZP:NTR-EGFP) female fish began at 28 days posthatching, the time at which oogenesis is initiated and is in its early stage, no mature oocytes formed in the Mtz-treated Tg(ZP:NTR-EGFP) female fish, and there were few oocytes stuck at the prefollicle primary growth stage (FIG. 3D). These results show that the blockade of oogenesis at the early stage by NTR-mediated catalysis of Mtz leads to undeveloped oocytes.

Oocyte Cell Death Induced by Mtz via Activation of Apoptosis

Figure 4:
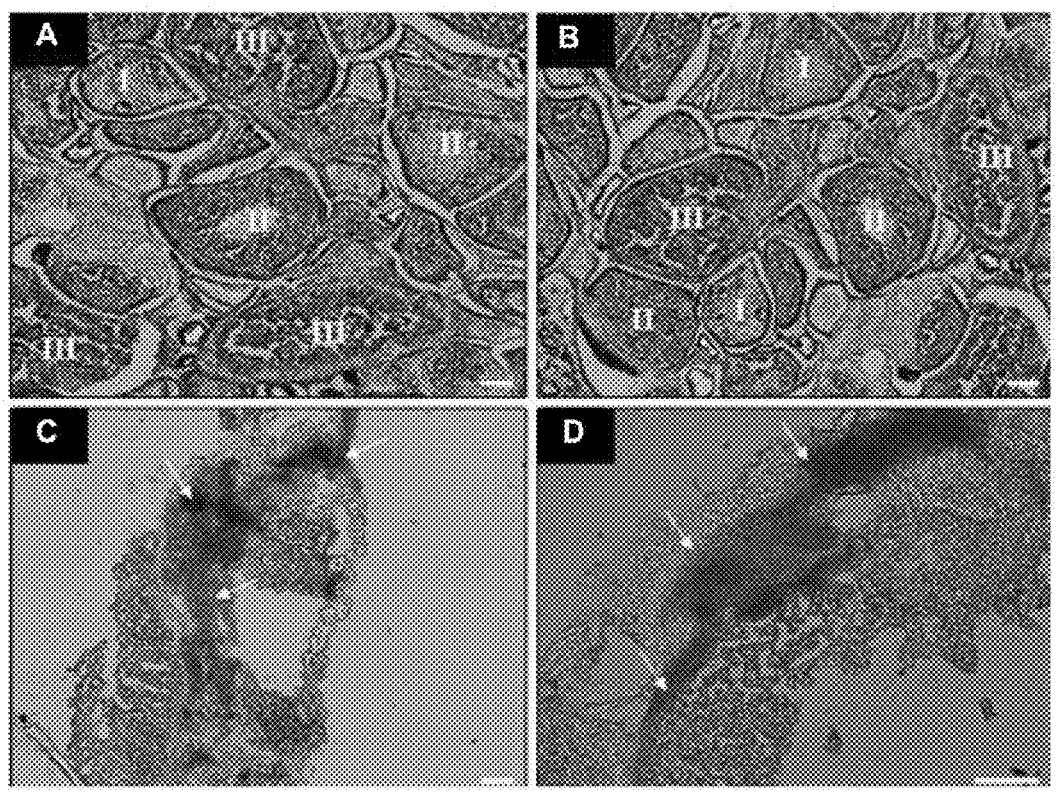
FIG. 4A is a photomicrograph showing a normal status of oocytes detected in a 3-month-old female AB stain zebrafish by a TUNEL cell death assay. The Roman numerals indicate the developmental stages of the oocytes. The white bar represents 100 μm.
FIG. 4B a photomicrograph showing a normal status of oocytes detected in a 3-month-old female Tg(ZP:NTR-EGFP) by a TUNEL cell death assay. The Roman numerals indicate the developmental stages of the oocytes. The white bar represents 100 μm.
FIG. 4C a photomicrograph showing an obvious signal of cell death (arrows indicated) induced by Mtz treatment as found in the gonads of a Mtz-treated 6-week-old Tg(ZP:NTR-EGFP) female fish. The oocyte cell death was induced by Mtz via apoptosis. The white bar represents 100 μm.
FIG. 4D is a photomicrograph showing an obvious signal of cell death (arrows indicated) induced by Mtz treatment as found in the gonads of a Mtz-treated 6-week-old Tg(ZP:NTR-EGFP) female fish. The oocyte cell death was induced by Mtz via apoptosis. The white bar represents 100 μm.

NTR/drug 5-(Aziridin-1-yl)-2,4-Dinitrobenzamide (CB1954), which is an analogue of Mtz, has been proposed as an agent for cancer gene therapy. Bacterial NTR converts the pro-drug CB1954 to an active drug, which thereby introduces interstrand cross-links into the DNA and leads to apoptosis via the activation of caspases 3, 8, and 9. These lesions kill dividing and non-dividing tumor cells, such as the SKOV3 ovarian carcinoma cell line as well as colon cancer cells. Mtz was chosen over CB1954 in this study due to its efficacy in destroying oocytes. In order to understand whether the mechanism of Mtz is similar to that of CB1954, which induces cell death via apoptosis, oocytes sectioned from adult female fish were evaluated by a TUNEL cell death assay. A significant signal of cell death was revealed in the ovaries of the adult Tg(ZP:NTR-EGFP) female fish with Mtz-induced atrophy (FIGS. 4C and 4D), whereas, a normal status for oocyte formation was shown in the AB strain zebrafish and the Tg(ZP:NTR-EGFP) fish (FIGS. 4A and 4B). These results show that Mtz-induced oocyte cell death at the early stage of oogenesis and led to gonadal dysgenesis.

Oocyte-Specific Catalysis of Mtz Regulates Activation of Ovarian Killer Gene

As indicated by the results presented in FIGS. 4C and D, NTR catalyzes the Mtz substrate to cause oocyte death predominantly via apoptosis. Members of the Bcl-2 gene family are critical mediators of apoptotic cell death. We detected members of the Bcl-2 gene family, including pro-apoptotic and anti-apoptotic genes, by real-time PCR, but only bok-1 and bok-2 are regulated by NTR/Mtz oocyte-specific mediated system (FIGS. 5A-5C). Bok, which is a proapoptotic member of the Bcl-2 family, was first isolated in a yeast two-hybrid screen of an ovarian cDNA library. It is also called the ovarian killer gene because of its primary expression in the reproductive tissues of mammals and zebrafish. Bok contains the Bcl-2 homology domain (BH-1, -2, and -3) and can induce apoptosis in a variety of cell types; however, this activity can be inhibited by heterodimerizing with Mcl-1. In the present study, expression of the antiapoptotic genes mcl-1a and mcl-1b is not affected by NTR/Mtz. Therefore, we assume that NTR/Mtz may mediate oocyte-specific cell death by disrupting the heterodimerization balance via activation of the bok ovarian killer gene.

Gonadal Dysgenesis Results in Infertility

A bloated ovary is an explicit feature in adult female zebrafish; however, this feature was non-existent in the Tg(ZP:NTR-EGFP) female fish after Mtz treatment. This phenomenon resulted from gonadal dysgenesis, and it might reduce reproductive capacity. In order to know whether the Mtz-treated transgenic Tg(ZP:NTR-EGFP) female fish are infertile, the number of fertilized eggs from the Mtz-treated Tg(ZP:NTR-EGFP) female fish and the AB strain male fish was used as a reference for the evaluation of reproductive capacity. In contrast to the normal spawning activity in the control groups, all of the Tg(ZP:NTR-EGFP) female fish with Mtz treatment lost spawning activity and became infertile (FIG. 5D). This result shows that reliable infertility of transgenic zebrafish can be achieved by a NTR/Mtz oocyte-specific mediated system.

Platform Technology of Infertility Control in Transgenic Ornamental Zebrafish

It is well known that zebrafish and medaka ornamental fish with exogenous fluorescent protein expression are the only two commercialized products of genetically modified aquatic animals to date. However, transgenic ornamental zebrafish that are able to reproduce will impede marketing and cause a decline in the price due to private breeding. In the present study, we established an inducible technology platform for the control of infertility, which can be immediately applied to transgenic ornamental zebrafish. The strategy for infertility control in ornamental zebrafish is shown in FIG. 6. Homozygous Tg(ZP:NTR-EGFP) female fish and homozygous transgenic ornamental male zebrafish were selected and crossed to generate progeny. The female progeny with EGFP expression in the gonads were screened at 28 days posthatching and then immersed in embryo medium containing 5 mM Mtz until the fish grew into adults. All of the adult transgenic ornamental zebrafish with Mtz treatment can be traded on the market, whereas, the breeders of the transgenic ornamental zebrafish can be maintained without Mtz treatment. The infertile platform strategy presented in this study not only has a high efficiency and can be easily manipulated, it also improves the disadvantages of traditional approaches for infertility, such as less than 100% reliability and irreversibility. We expect that the inducible platform developed in this work can be used as model of infertility control and will be applicable to other aquaculture fish species.

II. The Suicide Gene KillerRed

Materials and Methods

Zebrafish Line and Maintenance

AB strain zebrafish were purchased from the zebrafish international resource center and maintained in a freshwater recirculating aquarium with a controlled light cycle of 14 h light/10 h dark at 28° C. Zebrafish embryos, larvae, and adult fish were raised, maintained and crossed under standard laboratory conditions at 28° C. (Westerfield, 1995). The age of embryos and juveniles are indicated as hours post-fertilization (hpf) and days posthatching (dpf), respectively. The progeny crossed from AB strain were used for microinjections.

Construction of KillerRed Expression Construct

The Tol2 transposable element, which encodes a gene for a fully functional transposase capable of catalyzing transposition in zebrafish and improving the efficiency of germ-line transmission, was isolated from Japanese medaka fish (*Oryzias latipes*). The plasmid, pT2KXIGΔIN, including the expression cassette (Ef1α promoter, hrGFP gene, and SV40 polyadenylation) and flanking the expression cassette of the Tol2 antonomous transposon elements (500-bp left arm and 500-bp right arm), was kindly provided by Dr. Kawakami. The KillerRed gene (SEQ ID NO: 54) was amplified by PCR from plasmid pKillerRed-mem (Evrogen) using the forward primer KR(f) 5'-ACTACCGGTATGCTGTGCTGTATG-AGAAGAACC (SEQ ID NO: 50) and reverse primer KR (r) 5'-ACTATCGATTTAATCCTCGTCGCTACCGATGGCG (SEQ ID NO: 51). The forward and reverse primers was designed to create an AgeI and ClaI restriction site, respectively (underlined nucleotides). The KillerRed PCR product was digested AgeI and ClaI and then cloned directly into the same enzyme site in the pT2KXIGΔIN plasmid to replace hrGFP gene, and then generate a plasmid pT2-Ef1α-KillerRed. The 2.2-kb 5'-flanking region of the zona pellucida (zp3) gene, which is capable of driving oocyte-specific expression, was amplified by PCR from zebrafish genomic DNA using the forward primer zp3(f) 5'-AGTGG-GCCCAATAAATGTCTGAAACCTTATCTTTGGCTTTT (SEQ ID NO: 3) and the reverse primer zp3(r) 5'-ACT ACCGGTCCTTGAAGACTCAATGCCACAATGCTCATC (SEQ ID NO: 4) to create the ApaI and AgeI restriction enzyme sites, respectively (underlined nucleotides). The zp3 promoter PCR product was digested with ApaI and AgeI and cloned into downstream of the Tol2 transposon right arm of pT2-Ef1α-KillerRed to replace the ef1α promoter, thereby, generating the expression plasmid pT2-ZP-KillerRed.

Establishment of Tg(ZP:KillerRed) Transgenic Line

To generate stable Tg(ZP:KillerRed) line, 50 ng/µl of the pT2-ZP-KillerRed construct was co-microinjected with 50 ng/µl of capped Tol2 transposase mRNA into one-cell stage embryos. The pCS-TP plasmid encoding the Tol2 transposase was linearized with NotI and used as the template for in vitro transcription with mMessage mMachine (Ambion, Foster City, USA) according to the manufacturer's protocol. The injected embryos were incubated to adults and then crossed with the AB strain zebrafish to obtain offspring for the identification of a germ-line transmitted transgenic founder by detecting KillerRed expressions using a fluorescence microscopy. The F2 transgenic fish from intercrossed F1 transgenic fish were used in the experiment of light irradiation treatment.

Detection of Genomic Integration and KillerRed Expression

To screen the transgenic founders, the F1 offspring from each injected female fish were used for the detection of germ line transmission and KillerRed expression. The genomic DNA of F1 embryos were extracted as described previously. The total RNA was extracted from F1 embryos using TRIzol reagent (Invitrogen, USA). First-strand cDNA was synthesized in a 20 µl RT reaction from 1 µl of total RNA using the SuperScript III First-Strand kit (Invitrogen). The PCR was performed from genomic DNA and cDNA using the forward primer KR-id (f) 5'-ATGCTGTGCTGTATGAG AAGAACC (SEQ ID NO: 52) and the reverse primer KR-id (r) 5'-TTAATCCTCGTCGCTACCGAT GGCG (SEQ ID NO: 53), respectively, to detect the genomic integration and expression of KillerRed.

Light Irradiation Treatment

The intercrossed F2 progeny from the F1 Tg(ZP:NTR-EGFP) were collected and incubated at 28° C. in a Petri dish which covered with aluminum foil to avoid daylight irradiation. After 3 days incubation, the F2 embryos were incubated in an aquarium with a light cycle of 14 h light/10 h dark at 28° C. The F2 female Tg(ZP:KillerRed) with KillerRed expression were screened at 28 dpf using DsRed filter under a fluorescent microscopy and then irradiated for 1 hour using a FITC filter under a fluorescent microscopy (n=20/per tank; duplicate). Bulina et al. (2006), "Chromophore-assisted light inactivation (CALI) using the phototoxic fluorescent protein KillerRed" Nature Protocols, Vol. 1, No. 2, 947-953; Bulina et al., "A genetically encoded photosensitizer" (2006) *Nature, Biotechnology* Vol. 24, No. 1, 95-99; Pletnev et al., (2009) "Structural Basis for Phototoxicity of the Genetically Encoded Photosensitizer KillerRed" *THE JOURNAL OF BIOLOGICAL CHEMISTRY* VOL. 284, NO. 46, pp. 32028-32039, all of which are herein incorporated by reference in their entireties. The female Tg(ZP:KillerRed) without light irradiation was used as control (n=20 per tank; duplicate). The adult Tg(ZP:KillerRed) with/without light irradiation treatment were used to observe oocyte development by histological analysis and to evaluate the reproductive capacity.

Histological Analysis and Evaluation of Reproductive Capacity

Ovary tissues were harvested from adult zebrafish and fixed overnight in PBS buffer containing 4% paraformaldehyde (PFA) at 4° C. The samples were dehydrated in methanol and embedded in agarose. The samples were sectioned at 8 µm and then mounted on poly-L-lysine coated slides. The histological analysis was carried out by hematoxylin-eosin staining using standard protocols. To evaluate the reproductive capacity of female Tg(ZP:KillerRed) with light irradiation treatment, the fertilized egg of a female Tg(ZP:KillerRed) crossed with a male AB strain wild-type zebrafish was used as a reference.

Induction of Male Infertility in Genetically Modified Fish

Materials and Methods

In Silica Cloning

Human A-kinase anchoring protein-associated protein (Asp), outer dense fibers (Odf), and sperm acrosomal membrane-associated protein (Sam) amino acid sequences were obtained from NCBI (GeneBank accession numbers: AAG59587.1, NP_44510.2 and AAL83950.1). Zebrafish homologies of human Asp, Odf, and Sam were selected using the BLAT utility (http://www.ncbi.nlm.nih.gov/BLAST/Blast.cgi).

Detection of Testis-Specific Gene Expression in Embryonic and Adult Zebrafish by RT-PCR Total RNA was extracted from the brain, muscle, skin, fin, gill, heart, spleen, kidney, liver, pancreas, intestine, ovary, and testis using TRIzol (Invitrogen). Reverse transcription polymerase chain reaction (RT-PCR) was performed using a one-step RT-PCR kit (Invitrogen) with the PCR primers for zebrafish. Asp mRNA detection were (sense) 5'-CAA TAAG-GACACAGCCTCGTGATG-3' (SEQ ID NO: 27) and (antisense) 5'-CAGACTGCGAAACATGTG GAA AGG-3' (SEQ ID NO: 28), Odf mRNA detection, (sense) 5'-GTG AAACA-GAGAAGAAGCGTC CAG-3' (SEQ ID NO: 29) and (antisense) 5'-AGGAAGCGTGTATTTGTTTGGGGC-3' (SEQ ID NO: 30), and Sam mRNA detection, (sense) 5'-TATCTCGCAGTTGGTCATGGTCTG-3' (SEQ ID NO: 31) and (antisense) 5'-GCCGTATTAAAG CAACAGG-GAAGT-3' (SEQ ID NO: 32). The internal loading control was β-actin by (sense) 5'-GTCCCTGTACGCCTCTG-GTCG-3' (SEQ ID NO: 33) and (antisense) 5'-GCCGGACT- CATCGTACTCCTG-3' (SEQ ID NO: 34). The RT-PCR program consisted of one 30 min cycle at 50° C. and 2 min at 94° C., followed by PCR amplification with 35 cycles of 94° C. for 0.5 min, 56° C. for 0.5 min, 72° C. for 0.5 min, and a final extension of one cycle at 72° C. for 5 min. The RT-PCR products were then subjected to 2% agarose gel electrophoresis.

Cloning of Zebrafish Testis-Specific Gene Promoters

Promoter regions for zebrafish testis-specific genes, Asp, Odf, and Sam, were identified upstream of their most 5' exons of NCBI cDNAs BC081402, XM_687680, and XM_691331, respectively. The promoter regions were retrieved through the Genome Browser Gateway and aligned with the zebrafish genomic sequence clone (GeneBank accession number: AL627129 for Asp; NW_634200 for Odf; and CAAK01010030 for Sam) using the BLAT utility (http://www.ncbi.nlm.nih.gov/genome/seq/BlastGen/BlastGen.cgi?taxid=7955). The zebrafish genomic sequences were used for genomic PCR cloning of the testis-specific gene promoter regions. The oligonucleotides (5'-ATTGTCCT-GTCTCTACAGATT TGG-3' (SEQ ID NO: 35) with the sequence from the 2,088 bp upstream of the Asp translation initiation site were designed as a forward sense primer, and the oligonucleotide (5'-CGCTAGCCCCATCACT-TCACTTTGAGCTGT GTT-3' (SEQ ID NO: 36) complementary to the 24 bp upstream of the Asp translation initiation site was used as a reverse antisense primer for PCR. The oligonucleotides (5'-GACGAAAATACCATGCTA AAT-TGACCC-3' (SEQ ID NO: 37) with the sequence from the 2,028 bp upstream of the Odf translation initiation site were designed as a forward sense primer, and the oligonucleotide (5'-CGCTAG CCCCATGACCACATTTGAGACCGAAGG-TAA-3' (SEQ ID NO: 38) complementary to the 24 bp upstream of the Odf translation initiation site was used as a reverse antisense primer for PCR. The oligonucleotides (5'-TACAAAAAGAGA CCTAAAACCTAGAGG-3' (SEQ ID NO: 39) with the sequence from the 2,034 bp upstream of the Sam translation initiation site were designed as a forward sense primer, and the oligonucleotide (5'-CGCTAGC-CCCATGGTTTCTGC TGTAAATGAGCTAAG-3' (SEQ ID NO: 40) complementary to the 24 bp upstream of the Sam translation initiation site was used as a reverse antisense primer for PCR. The proximal promoter regions were then sequenced for verification based on 5' sequences from the cDNA sequences. Transcriptional factor binding sites were predicted by using Match program (http://www.generegulation.com/pub/programs.html#match). The database is TRANSCompel 6.0.

Whole-Mount In Situ Hybridization

Based on the RT-PCR screen for the onset of Asp, Odf, and Sam expression in developing zebrafish (see previous discussion), 21-30 days postfertilization (dpf) larvae were collected and prepared for whole-mount in situ hybridization. The zebrafish were incubated in a hybridization solution containing sense or antisense digoxigenin probes generated using the Maxiscript kit (Ambion Inc., Austin, Tex., USA). Larvae were washed extensively to remove the unbound probe, blocked in 2 mg/ml BSA, 5% goat serum, 5% dimethyl sulfoxide, and PBS containing 0.01% Tween 20 and then incubated overnight at 4° C. in blocking solution containing anti-digoxigenin antibody conjugated to alkaline phosphatase (Roche). After extensive washing in NTMT [100 mm NaCl, 100 mm Tris-HCl (pH 9.5), 50 mm MgCl2, and 0.1% Tween 20], larvae were incubated in BM Purple (Roche). After the color reaction, larvae were fixed in PBS containing 4% paraformaldehyde, transferred to methanol and then cleaned in benzylbenzoate/benzyl alcohol before examination by a differential interference contrast microscopy. Photomicrographs were taken using a Wild MPS52 camera (Leica, Canada) mounted on a DMRBE microscope (Leica), and images were also captured with a digital camera.

Generation and Maintenance of Transgenic Zebrafish

The 2,088 bp Asp, 2,028 bp Odf, and 2,034 bp Sam genomic PCR products generated from zebrafish genomic DNA were ligated into a pEGFP-C1 vector (Clontech). The resulting plasmids were named pASP-eGFP, pODF-eGFP, and pSAM-eGFP. Bacterial Ntr enzyme cDNA (GeneBank accession number U07860; SEQ ID NO: 46) was separately ligated into the 3' end of GFP of pASP-eGFP, pODFeGFP, and pSAM-eGFP, and the resulting plasmids were named pASP-eGFP:Ntr, pODF-eGFP:Ntr, and pSAM-eGFP:Ntr. To generate the transgenic zebrafish lines, the pASP-eGFP:Ntr, pODF-eGFP:Ntr, and pSAM-eGFP:Ntr plasmids were linearized by digesting the vector backbone with Sfi I and Not I. Digested DNA was adjusted to 100 ng/μl in 5 mM Tris (pH 7.5), 0.5 mM EDTA, 100 mM KCL, and 0.1% phenol red. For transgenic expression, approximately 200 pl of the DNA solution was then injected into the blastomere of early one-cell stage embryos using a glass micropipette. Adult zebrafish were obtained from a local aquarium-supply store and maintained at our own facility in a controlled environment with a 14/10-h light-dark cycle at 28° C. The fish spawned soon after light onset, and fertilized eggs were collected at the one-cell stage. The nucleotide sequences of Asp, Odf and Sam promoter regions are SEQ ID NOs: 47, 48 and 49, respectively.

Quantification of the Transcript of eGFP:Ntr Transgene in Transgenic Zebrafish

A quantitative real-time reverse transcriptase polymerase chain reaction (Q-rt-PCR) quantified the transcription of the eGFP:Ntr transgene. Zebrafish hepatic RNA was isolated using Trizol® Reagent (Invitrogen, USA) and followed by an RNeasy Mini Kit (Qiagen, Germany). A total of 20 μg of total RNA from each sample was treated with DNAfree® (Ambion, Austin, Tex.; USA) to eliminate genomic DNA contamination. A 2 μg sample of DNase-treated RNA was then reverse transcribed into cDNA using an iScript cDNA Synthesis Kit (BioRad, Hercules, Calif., USA) following the manufacturer's instructions. For real-time quantitative PCR reactions, serial dilutions of cDNA were made in TE buffer (10 mM Tris-HCl, 1 mM EDTA pH 8.0) and 2× LightCycler 480 SYBR Green 1 Master Reagents in a Roche LightCycler480 System. The cycling conditions were as follows: 2 min at 50° C. and 10 min at 95° C., followed by 45 cycles of 10 s at 95° C., 5 s at 60° C., and 7 s at 72° C. FIG. 7A shows that the primers G-for (5'-CACTACCTGAGCACCCAGTC-CGCC-3' (SEQ ID NO: 41) and N-rev (5'-GGATTTGGCAA-CACGCGCTTTACC-3' (SEQ ID NO: 42) were used to detect eGFP:Ntr fusion.

Development of Compound Transgenic Lines

To generate compound transgenic lines, the homozygous transgenic zebrafish of each line, Tg(Asp-eGFP:Ntr), Tg(Odf-eGFP:Ntr), and Tg(Sam-eGFP:Ntr), were then crossed with each other to generate double transgenic fish, Tg(AO-eGFP:Ntr)[Tg(Asp-eGFP:Ntr);Tg(Odf-eGFP:Ntr)], Tg(AS-eGFP:Ntr)[Tg(Asp-eGFP:Ntr);Tg(Sam-eGFP:Ntr)], and Tg(OS-eGFP:Ntr)[Tg(Odf-eGFP:Ntr);Tg(Sam-eGFP:Ntr)] and triple-transgenic fish, Tg(AOS-eGFP:Ntr)[Tg(Asp-eGFP:Ntr; Odf-eGFP:Ntr;Sam-eGFP:Ntr)] for experiments. RT-PCR was performed to test the expression of eGFP:Ntr in the testes of all lines. Animals from each cross were divided into four groups based on genotype. The four groups were then used to assess fertility in response to Met administration.

Metronidazole Dependent Cell Ablation

Metronidazole (Met, M3761, Sigma) was dissolved in a standard zebrafish embryo medium with vigorous agitation. Embryos were incubated at 28° C. in the dark, and 14-21 dpf transgenic embryos were used to study the dose response of Met in ablating gonad. In initial studies, 14 dpf embryos were incubated in a range of Met concentrations (1-10 mM). After a day interval of Met treatment for 1 week, a concentration of only 5 mM resulted in a complete loss of fluorescence. A concentration of 5 mM was used in all later studies and showed no deleterious effects on the 14 dpf larvae.

Fertility Assessment

Fertility was assessed by pairing each heterozygous transgenic fish with a WT mate. At least 20 transgenic fish were tested for each line, and the numbers of fertile zebrafish were compared with wild-type fish. Each male was assessed with multiple females. Zebrafish were labeled infertile if they were unable to produce offspring over a 4-month period.

Histological Analysis

Histological sections of zebrafish were fixed for 24 h in 10% neutral-buffered formalin, transferred to 70% ethanol, and embedded in paraffin. Sections were cut 5-mm thick and mounted on salinated slides for H&E staining. Histological sections were examined using a DM 5000 B fluorescence microscope (Leica Microsystems, Wetzlar, Germany) equipped with the CoolSNAP™ CCD camera (Roper Scientific, Tucson, Ariz., USA).

Results

Characterization and In Silico Cloning of Zebrafish Asp, Odf, and Sam Protein and Putative Promoter Sequences To identify zebrafish orthologues of A-kinase anchoring protein-associated protein (Asp), outer dense fibers (Odf), and sperm acrosomal membrane-associated protein (Sam), we undertook an Ensembl database blastp search (WU BLAST 2.0, default settings) comparing the human orthologue protein sequence against the zebrafish peptide library. This search produced significant hits. To compare the sequences and infer the relationship of zebrafish Asp, Odf, and Sam with other vertebrate orthologues, we performed amino acid sequence alignment and pairwise identification. Compared to the human, mouse, and rat orthologue, the amino acid sequence identities of Asp is 48.5%, Odf is 36.4%, and Sam is 26.2%, respectively (Chia-Chun Hsu et al. (2009) "Inducible Male Infertility by Targeted Cell Ablation in Zebrafish Testis" Marine Biotechnol, Springer New York, DOI 10.1007/s10126-009-9248-4, which is herein incorporated by reference in its entirety). Comparison of the zebrafish cDNA sequence of Asp, Odf, and Sam against the zebrafish genome database (http://www.sanger.ac.uk/Projects/D_rerio) has also allowed us to define the 5' upstream sequences of Asp, Odf, and Sam putative promoter region from AL627129, NW_634200, and CAAK01010030, respectively.

Figure 9:
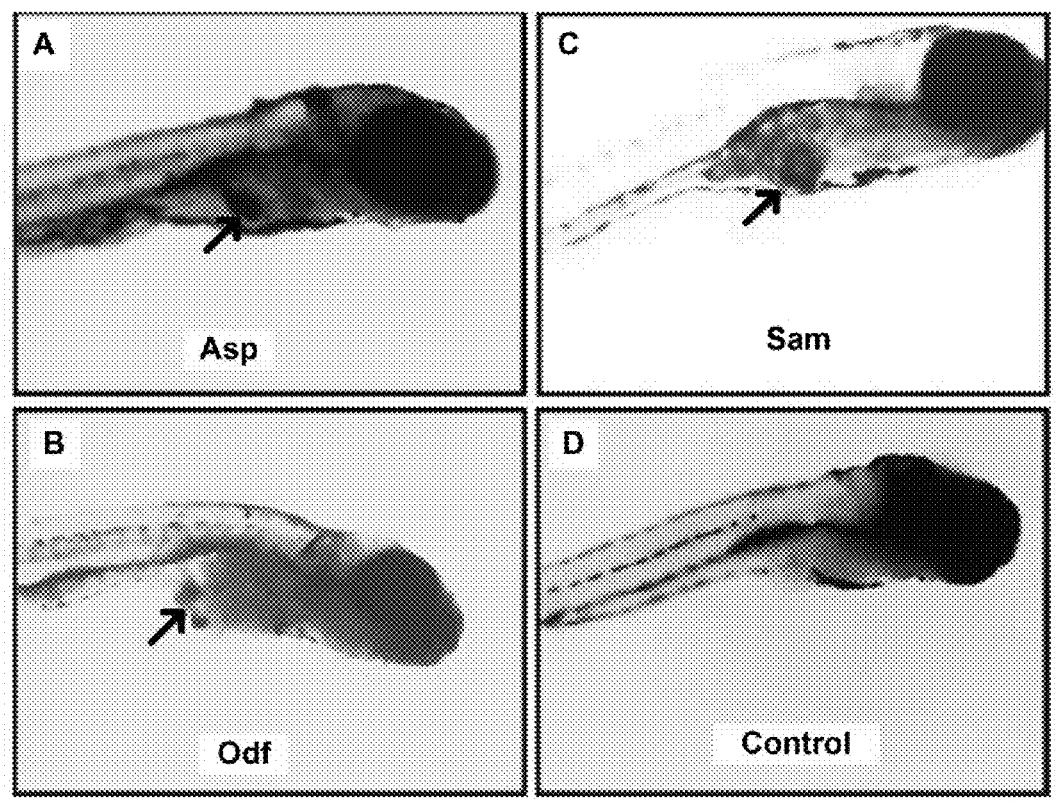

To characterize the regulatory regions of the zebrafish Asp, Odf, and Sam genes for transgenesis, we isolated the 2,088, 2,034, and 2,028 bp of 5' upstream sequences from the Asp, Odf, and Sam start codon, respectively. Program analysis of the 5' upstream sequences identified several spermatogenic or testicular transcription factor binding sites in the Asp, Odf, and Sam putative promoter regions (Hsu et al., ibid.). We investigated spatial and temporal expression of zebrafish Asp, Odf, and Sam mRNA during zebrafish development. Because Asp, Odf, and Sam are the three major classes of testis-specific (spermatocyte specific) genes used in this study, they play important roles in male reproduction, and it is interesting to compare their ontogenetic expressions during development. This study analyzes the spatial and temporal expression of the zebrafish Asp, Odf, and Sam genes during zebrafish development using a combination of RT-PCR and whole-mount in situ hybridization approaches. The temporal expression profiles of zebrafish Asp, Odf, and Sam mRNA were first examined by a RT-PCR assay. FIG. 8A shows that the maternal Asp, Odf, and Sam mRNA was detected at early embryonic stages and endogenous regulatory expression of Asp, Odf, and Sam was seen at larval stages of 3-7 dpf. The regulatory de novo expression of Asp, Odf, and Sam was seen at late larval and fry zebrafish. To determine whether or not the Asp, Odf, and Sam play a role in zebrafish testes, total RNAs were also extracted from different zebrafish tissues and analyzed by RT-PCR. The Asp and Sam genes were strongly expressed only in the testes, while the Odf gene was slightly expressed in the testes (FIG. 8B). To provide additional evidence that Asp, Odf, and Sam-positive cells are expressed in juvenile testis-like primordia, in situ hybridization analysis showed that those genes only played a role in the undifferentiated testis-like tissue in the juvenile stages of 21 days post fertilization (dpf; FIG. 9). The data indicates that Asp, Odf, and Sam played a role in testis development in growing zebrafish.

Generation of eGFP:Ntr Transgenic Zebrafish

To generate stable eGFP:Ntr expression in the zebrafish testis, the pASP-eGFP:Ntr, pODF-eGFP:Ntr, and pSAMeGFP:Ntr constructs were used to produce germline transmitting transgenic zebrafish lines (FIG. 7A). Transgenic fish were produced by microinjecting these constructs with plasmid vector sequences removed into one-cell stage zebrafish embryos. The injected embryos were examined at 21-30 dpf by fluorescence microscopy, grouped according to the intensity of fluorescence, raised to sexual maturity, and screened for potential founders. The founder fish were mated with WT fish and the fluorescence of their 21-30 dpf progeny was examined using fluorescence microscopy. We raised the embryos injected with those constructs and isolated nine F0 transgenic founders. The F2 inheritance rates in all the nine lines were consistent with those expected for Mendelian segregation and with rates described in previous studies. Using a Q-rt-PCR, we compared the amount of residual eGFP:Ntr RNA that could be detected within these transgenic zebrafish lines (FIG. 8B). To assess whether or not the transgene conferred testis-specific expression, we compared the expression of Asp, Odf, and Sam and the eGFP:Ntr transgene in various adult tissues of Tg(Asp-eGFP:Ntr)#2, Tg(Odf-eGFP:Ntr)#3, and Tg(Sam-eGFP:Ntr)#1. Zebrafish eGFP:Ntr mRNA was expressed in the testes and was not detected in other organs or tissues including muscle, liver, kidney, pancreas, intestine, and ovaries (FIG. 7C). In addition, the proportion of expression level of the eGFP:Ntr transgene was very similar to that of their endogenous Asp, Odf, and Sam genes (FIG. 8B). Moreover, GFP-expressing testes were visible through the body wall of a 28-dpf of Tg(Asp-eGFP:Ntr) male fish, a 21-dpf of Tg(Odf-eGFP:Ntr) male fish, and a 36-dpf of Tg(Sam-eGFP:Ntr) male fish (FIG. 10). Three stable transgenic lines, Tg(Asp-eGFP:Ntr)#2, Tg(Odf-eGFP:Ntr)#3, and Tg(Sam-eGFP:Ntr)#1, were developed with overexpression of higher levels of the eGFP:Ntr. These lines were redesignated as Tg(Asp-eGFP:Ntr), Tg(Odf-eGFP:Ntr), and Tg(Sam-eGFP:Ntr), respectively.

Fertility Studies of Tg(Asp-eGFP:Ntr), Tg(Odf-eGFP:Ntr), and Tg(Sam-eGFP:Ntr)

To assess the fertility of Met-treated transgenic zebrafish lines, Tg(Asp-eGFP:Ntr), Tg(Odf-eGFP:Ntr), and Tg(Sam-eGFP:Ntr) lines were crossed with wild-type zebrafish (100-200 eggs per line; three mating pairs per line). The reproductive parameters were compared with wild-type pairs of the same strain (100-200 eggs per five mating pairs). Although all transgenic lines and wild-type lines remained fertile before Met treatment, the frequency of infertility of transgenic male lines was significantly higher than that of the transgenic female and wild-type (Table 1). In fact, the infertility of Met-treated Tg(Asp-eGFP:Ntr) transgenic males mated with wild-type female fish increased by over 68.0% compared to that of wild-type. Similarly, the infertility of Met-treated Tg(Odf-eGFP:Ntr) and Tg(Sam-eGFP:Ntr) transgenic males mated with wild-type female fish was increased by over 59.1% and 54.1% compared to that of wild type. However, Met-treated transgenic female lines remained fertile as wild-type female.

TABLE 1

| Gender lines | Female infertility | | Male infertility | |
|---|---|---|---|---|
| | Met− | Met+ | Met− | Met+ |
| Tg (Asp-EGFP:Ntr) | 0/25 (0%) | 0/25 (0%) | 0/25 (0%) | 17/25 (68.0%) |
| Tg (Odf-EGFP:Ntr) | 0/22 (0%) | 0/22 (0%) | 0/22 (0%) | 13/22 (59.1%) |
| Tg (Sam-EGFP:Ntr) | 0/24 (0%) | 0/24 (0%) | 0/24 (0%) | 13/24 (54.1%) |
| Wild type | 0/28 (0%) | 0/28 (0%) | 0/28 (0%) | 0/28 (0%) |

Male Infertility of Compound eGFP:Ntr Transgenic Lines

After establishing breeding colonies of these three transgenic lines, Tg(Asp-eGFP:Ntr), Tg(Odf-eGFP:Ntr), and Tg(Sam-eGFP:Ntr), it became clear that the male transgenic fish were at intermediate levels of infertility while the female transgenic fish remained fertile after Met treatment. None of the Met-treated adult males crossed with wild-type females were fully successful in spawning fertilized eggs (Table 1). Table 1 shows the results of fertility studies of triggering infertility in Tg(Asp-eGFP:Ntr), Tg(Odf-eGFP:Ntr), and Tg(Sam-eGFP:Ntr) transgenic zebrafish lines by 5 mM Met after every other day of Met treatment for 1 week. To reach high or full (100%) levels of male infertility in Met-treated transgenic zebrafish lines, we generated compound transgenic lines, Tg(AO-eGFP:Ntr), Tg(AS-eGFP:Ntr), Tg(OS-eGFP:Ntr), and Tg(AOS-eGFP:Ntr) by crossing each other of Tg(Asp-eGFP:Ntr), Tg(Odf-eGFP:Ntr), and Tg(Sam-eGFP:Ntr), then examined male infertility after Met treatment (Table 2). At 4 months of age, Met-treated compound transgenic males had three mediate (76.4%), intermediate high (85.7%), high (95.0%), and full (100%) levels of infertility for Tg(OS-eGFP:Ntr), Tg(AO-eGFP:Ntr), Tg(AS-eGFP:Ntr), and Tg(AOS-eGFP:Ntr), respectively. Met-treated compound transgenic females crossed with wild-type zebrafish remained fertile. No gross abnormalities were apparent in any of the Met-untreated compound transgenic zebrafish lines or Met-treated double transgenic females. However, some male triple-transgenic fish of Tg(AOS-eGFP:Ntr) occasionally died after 5 m Met treatment for 1 week. Depuration studies found no recovery in reproductive capacity in Tg(OS-eGFP:Ntr), Tg(AO-eGFP:Ntr), Tg(AS-eGFP:Ntr), and Tg(AOS-eGFP:Ntr) fish after Met treatment. Table 2 shows the results of fertility studies of triggering infertility in compound transgenic zebrafish Tg(AO-eGFP:Ntr), Tg(AS-eGFP:Ntr), Tg(OS-eGFP:Ntr), and Tg(AOS-eGFP:Ntr) by 5 mM Met after every other day of Met treatment for 1 week.

TABLE 2

| Gender lines | Female infertility | | Male infertility | |
|---|---|---|---|---|
| | Met− | Met+ | Met− | Met+ |
| Tg (AO-EGFP:Ntr) | 0/35 (0%) | 0/35 (0%) | 0/35 (0%) | 30/35 (85.7%) |
| Tg (AS-EGFP:Ntr) | 0/40 (0%) | 0/40 (0%) | 0/40 (0%) | 38/40 (95.0%) |
| Tg (OS-EGFP:Ntr) | 0/34 (0%) | 0/34 (0%) | 0/34 (0%) | 26/34 (76.4%) |
| Tg (AOS-EGFP:Ntr)[a] | 0/38 (0%) | 0/38 (0%) | 0/38 (0%) | 38/38 (100%) |
| Wild type | 0/30 (0%) | 0/30 (0%) | 0/30 (0%) | 0/30 (0%) |

[a]Male triple-transgenic fish, Tg(AOS-EGFP:Ntr), will occasionally cause a lethal problem after 5 mM Met treatment for 1 week.

Aberrant Spermatogenesis in Met-Treated Transgenic Zebrafish Male

We next examined whether or not the spermatogenesis or morphology of the eGFP:Ntr transgenic lines were disturbed by Met treatment and whether or not any such changes could explain the observed infertility. Therefore, testis sections from wild type and different eGFP:Ntr transgenic lines were examined. In general, some germ cells were still able to go through both meiotic divisions, and a few mature sperm were found in some compound transgenic fish with Met treatment. No gross abnormalities were apparent in the bodies of these male transgenic lines. However, wild-type zebrafish presented normal morphology with all sperm maturation stages visible during spermatogenesis, and only very low counts of spermatids and spermatozoa were observed in the testes of Met-treated eGFP:Ntr transgenic lines. Moreover, Met-treated compound transgenic lines Tg(OS-eGFP:Ntr), Tg(Tg(AO-eGFP:Ntr), and Tg(AS-eGFP:Ntr) bred to 4 months were near infertility and displayed an arrest in spermatogenesis at metaphase I. The Met-treated Tg(AS-eGFP:Ntr) and Tg(AO-eGFP:Ntr) fish showed only a few spermatozoa (SPERM) and most of spermatogonia appeared at different mitotic divisions (SPG) in a testis cross section. The Met-treated Tg(OS-eGFP:Ntr) fish exhibited less effect in the testis than that of Tg(AS-eGFP:Ntr) and Tg(AO-eGFP:Ntr) lines compared to WT zebrafish (FIG. 11A and Table 2). Particularly, older Tg(AOS-eGFP:Ntr) fish (≧6 months) had very small and withered testes, and virtually all traces of spermatogenesis disappeared and all tubules were devoid of germ cells in all these compound transgenic fish (FIG. 11B). Significantly, even though the Tg(AOS-eGFP:Ntr) males lacked functional testes, they showed male-pattern reproductive behavior, inducing the spawning act and competing with healthy males to disrupt fertilization (FIG. 11C). Because spermatogonia were not evident in the older transgenic zebrafish with Met treatment, it seems likely that their destruction was caused by transgenic eGFP:Ntr expression after Met treatment rather than by the transgene expression or other unknown effects.

Discussion

This study applied the Ntr/Met ablation technique, which is an inducible system for inducing cell death that requires both the Ntr enzyme and prodrug Met. We produced transgenic zebrafish in which the eGFP:Ntr is expressed under the control of the spermatocyte-specific Asp, Odf, and Sam promoters. Whereas, female animals appear completely normal, males that carry the eGFP:Ntr have very small testes, and germ cells are deficient or absent in eGFP:Ntr lines. This study shows that the proposed Ntr/Met system can be used to applicably ablate germ cell populations in zebrafish testis, resulting in infertility in male zebrafish. No genetic tool had previously been established that allows one to conditionally ablate a target cell population in zebrafish testis. While several techniques have been directed toward specific cell ablation in zebrafish testis, they have all presented considerable limitations in application. Full infertility in the Tg(AOS-eGFP:Ntr) line and high infertility in the Tg(AS-eGFP:Ntr) line after Met treatment was due to greatly disturbed spermatogenesis, with males having either no functional or undifferentiated testes (FIGS. 11A and 11B). Further, there were no or very few counts of spermatids and spermatozoa in their testes. For the partially infertile eGFP:Ntr lines (low and medium, intermediate high infertility), developing testis were easily visible during spermatogenesis, and the various counts of spermatids and spermatozoa were observed in the testes of those eGFP:Ntr transgenic lines (FIG. 11B). Given the inducible cytotoxic potential of the Ntr/Met system in previous studies, the phenotypes of the eGFP:Ntr zebrafish show that the expression of the transgene was effectively silenced in all cellular environments except the male germ line. Although RT-PCR analysis of tissue specificity (FIG. 7C) and in vivo GFP signals located the eGFP:Ntr in the testes of eGFP:Ntr lines, it is difficult to eliminate the possibility of some ectopic expression because it is impractical to examine every tissue for the trace presence of protein or mRNA. The restricted effect of this toxicity after Met treatment on the male germ line emphasizes the absolute testis specificity of the ~2 kb Asp, Odf, and Sam promoter region. In addition, transgenic expression from the only ~2 kb of Asp, Odf, and Sam 5' upstream sequence used as the transcriptional control region in our construct may not accurately reproduce the quantitative expression of their natural genes; some nuclear event must occur during maturation of the primitive spermatogonia that leads to transgene activation. Although program analysis of the 5' upstream sequences identified several spermatogenic or testicular transcription factor binding sites in the Asp, Odf, and Sam putative promoter regions (Hsu et al. ibid.), the regulatory control of the Asp, Odf, and Sam promoter regions remains to be further investigated. We do not fully understand the factors that so dramatically restrict its expression in zebrafish testis in the current study.

Another zebrafish model was recently developed to target cell ablation in zebrafish and was applied to the primordial germ cells (PGCs). That zebrafish model is based on the bicistronic protein killer bacterial system parD. Preferential expression of the toxin kid in the PGCs and concomitant expression of the natural antidote kis allowed specific ablation of the PGCs. The zebrafish model shows that zebrafish embryos depleted of germ cells develop into sterile male fish. However, this parD/kis zebrafish system uses laborious and time-consuming ablation methods. Moreover, this system is not able to generate genetic inheritable animals. In a genetic inheritable system, cell death is induced by expressing the M2(H37A) toxic ion channel of the influenza A virus in the target cell population of *Xenopus* embryos. This toxic effect can be inhibited by adding the antiviral drug rimantadine in mammalian cell cultures and *Xenopus* embryos but not transgenic mice. However, the establishment and maintenance of stable transgenic lines often requires long-term exposure to the inhibitor. The eGFP:Ntr lines in this study demonstrate that a tight expression control of the combined genetic and pharmacological system is a major advantage as it allows germline transmission and generation of stable Ntr-expressing transgenic lines. The availability of stable transgenic lines allows the design and execution of reproducible testis ablation assays in other species. In addition, this genetic tool will be of particular usefulness when it is necessary to ablate cells in a large number of animals as it provides large-scale reproducibility in infertile experimental animals.

In summary, this study generated inducible sterility zebrafish male models in which the developing testes are totally or partially damaged, leading to asexual healthy adult zebrafish. This study is practically useful for fish ecology. The prevention of escaping GMF in natural environments can be effected by the fact that infertile males are able to mate with WT females, thereby, producing unfertilized eggs, leading to a rapid decrease in the population size of GMF. When required, the system for ablating the testis tissue could be used for generating GMF whose fertility can be controlled by apoptosis. This system could be valuable in preventing the contamination of wild-type fish populations with GMF, which represents a major argument for applying GMF in the aquaculture.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A genetically modified (GM) fish whose genome comprises a fusion transgene operably linked to a fish gonad-specific promoter, wherein the fusion transgene comprises:
   (a) a nitroreductase (NTR)-encoding gene, and
   (b) a reporter gene operably linked to the nitroreductase (NTR)-encoding gene, wherein the fish gonad-specific promoter is selected from the group consisting of a fish ovary-specific promoter and a fish testis-specific promoter, wherein a female of the GM fish expresses the fusion transgene that is operably linked to the ovary-specific promoter and a male of the GM fish expresses the fusion transgene that is operably linked to the testis-specific promoter, and further wherein treatment with a NTR-activated cytotoxic prodrug induces infertility of the female of the GM fish and increases frequency of infertility of a homozygous male of the GM fish as compared to that of a wild counterpart.

2. The GM fish of claim 1, wherein the fish ovary-specific promoter is a zp2 promoter.

3. The GM fish of claim 1, wherein the GM fish is a female treated with a NTR-activated cytotoxic prodrug and exhibits infertility.

4. The GM fish of claim 1, wherein the fish gonad-specific promoter comprises a fish ovary-specific promoter.

5. The GM fish of claim 4, wherein the fish ovary-specific promoter is selected from the group consisting of zp2 and zp3 promoters.

6. The GM fish of claim 1, wherein the fish gonad-specific promoter comprises a fish testis-specific promoter.

7. The GM fish of claim 6, wherein the fish testis-specific promoter is selected from the group consisting of Asp, Odf and Sam promoters.

8. The GM fish of claim 6, wherein the GM fish is a male having been treated with a reductase-activated prodrug and exhibits an increased probability of infertility.

9. The GM fish of claim 1, which is a female.

10. The GM fish of claim 3, which exhibits an ovary atrophy phenotype.

11. The GM fish of claim 4, wherein the fish ovary-specific promoter comprises zp3 promoter.

12. The GM fish of claim 1, wherein the GM fish comprises a GM zebrafish.

13. The GM fish of claim 1, which is a female, wherein the treatment of the NTR-activated cytotoxic prodrug causes oocyte cell death and elimination of the reporter gene's expression in the gonads thereof.

14. The GM fish of claim 13, which is homozygous.

15. A method of generating an infertile GM fish with a phenotype and/or genotype of interest comprising the steps of
   (a) providing a homozygous male of a transgenic fish with a phenotype and/or genotype of interest;
   (b) providing the GM fish of claim 14;
   (c) causing the GM fish from step (b) to mate with the transgenic fish with the phenotype and/or genotype of interest from step (a) to produce a progeny;
   (d) selecting the progeny that is a female and expresses the reporter gene in the gonad; and
   (e) treating the selected female progeny with a therapeutically effective amount of a NTR-activated cytotoxic prodrug and thereby generating an infertile GM fish with the phenotype and/or genotype of interest.

16. The method of claim 15, wherein the GM fish in step b) comprises a GM zebrafish.

17. The method of claim 16, wherein the homozygous male in step a) comprises a male ornamental zebrafish and the GM fish in step b) comprises a GM zebrafish.

\* \* \* \* \*

SEQUENCE LISTING

<160> NUMBER OF SEQ ID NOS: 54

<210> SEQ ID NO 1
<211> LENGTH: 33
<212> TYPE: DNA
<213> ORGANISM: Artificial Sequence
<220> FEATURE:
<223> OTHER INFORMATION: Forward Primer ntr(f)

<400> SEQUENCE: 1
actaccggta tggatatcat ttctgtcgcc tta                           33

<210> SEQ ID NO 2
<211> LENGTH: 35
<212> TYPE: DNA
<213> ORGANISM: Artificial Sequence -continued

```
<220> FEATURE:
<223> OTHER INFORMATION: Reverse Primer ntr(r)

<400> SEQUENCE: 2
actaccggtg tcacttcggt taaggtgatg ttttg                          35

<210> SEQ ID NO 3
<211> LENGTH: 41
<212> TYPE: DNA
<213> ORGANISM: Artificial Sequence
<220> FEATURE:
<223> OTHER INFORMATION: Forward Primer zp3(f)

<400> SEQUENCE: 3
agtgggccca ataaatgtct gaaaccttat ctttggcttt t                   41

<210> SEQ ID NO 4
<211> LENGTH: 39
<212> TYPE: DNA
<213> ORGANISM: Artificial Sequence
<220> FEATURE:
<223> OTHER INFORMATION: Reverse Primer zp3(r)

<400> SEQUENCE: 4
actaccggtc cttgaagact caatgccaca atgctcatc                      39

<210> SEQ ID NO 5
<211> LENGTH: 24
<212> TYPE: DNA
<213> ORGANISM: Artificial Sequence
<220> FEATURE:
<223> OTHER INFORMATION: Forward Primer ntr-id (f)

<400> SEQUENCE: 5
atggatatca tttctgtcgc ctta                                      24

<210> SEQ ID NO 6
<211> LENGTH: 27
<212> TYPE: DNA
<213> ORGANISM: Artificial Sequence
<220> FEATURE:
<223> OTHER INFORMATION: Reverse Primer egfp (r)

<400> SEQUENCE: 6
ttacttgtac agctcgtcca tgccgag                                   27

<210> SEQ ID NO 7
<211> LENGTH: 20
<212> TYPE: DNA
<213> ORGANISM: Artificial Sequence
<220> FEATURE:
<223> OTHER INFORMATION: Forward Primer bcl-2 forward

<400> SEQUENCE: 7
tggcgtccca ggtagataat                                           20

<210> SEQ ID NO 8
<211> LENGTH: 20
<212> TYPE: DNA
<213> ORGANISM: Artificial Sequence
<220> FEATURE:
<223> OTHER INFORMATION: Reverse Primer bcl-2 reverse

<400> SEQUENCE: 8
accgtacatc tccacgaagg                                           20
```

```
<210> SEQ ID NO 9
<211> LENGTH: 20
<212> TYPE: DNA
<213> ORGANISM: Artificial Sequence
<220> FEATURE:
<223> OTHER INFORMATION: Forward Primer bcl-xl forward

<400> SEQUENCE: 9
ggcttgtttg cttggttgac                                              20

<210> SEQ ID NO 10
<211> LENGTH: 19
<212> TYPE: DNA
<213> ORGANISM: Artificial Sequence
<220> FEATURE:
<223> OTHER INFORMATION: Reverse Primer bcl-xl reverse

<400> SEQUENCE: 10
tggtgcaatg gctcatacc                                               19

<210> SEQ ID NO 11
<211> LENGTH: 22
<212> TYPE: DNA
<213> ORGANISM: Artificial Sequence
<220> FEATURE:
<223> OTHER INFORMATION: Forward Primer mcl-1a forward

<400> SEQUENCE: 11
ggatcctcaa aaacaagagc tg                                           22

<210> SEQ ID NO 12
<211> LENGTH: 23
<212> TYPE: DNA
<213> ORGANISM: Artificial Sequence
<220> FEATURE:
<223> OTHER INFORMATION: Reverse Primer mcl-1a reverse

<400> SEQUENCE: 12
catgacggac aacagactct aca                                          23

<210> SEQ ID NO 13
<211> LENGTH: 19
<212> TYPE: DNA
<213> ORGANISM: Artificial Sequence
<220> FEATURE:
<223> OTHER INFORMATION: Forward Primer mcl-1b forward

<400> SEQUENCE: 13
gcacgagctc gcttacaaa                                               19

<210> SEQ ID NO 14
<211> LENGTH: 20
<212> TYPE: DNA
<213> ORGANISM: Artificial Sequence
<220> FEATURE:
<223> OTHER INFORMATION: Reverse Primer mcl-1b reverse

<400> SEQUENCE: 14
ctctgttgcc acttgcttga                                              20

<210> SEQ ID NO 15
<211> LENGTH: 20
<212> TYPE: DNA
<213> ORGANISM: Artificial Sequence
<220> FEATURE:
<223> OTHER INFORMATION: Forward Primer bax-1 forward
```

```
<400> SEQUENCE: 15
gcccgtgaga tcttctctga                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse Primer bax-1 reverse

<400> SEQUENCE: 16
tcaggaaccc tggttgaaat                                               20

<210> SEQ ID NO 17
<211> LENGTH: 20
<212> TYPE: DNA
<213> ORGANISM: Artificial Sequence
<220> FEATURE:
<223> OTHER INFORMATION: Forward Primer bax-2 forward

<400> SEQUENCE: 17
gttcacagat ggccagatca                                               20

<210> SEQ ID NO 18
<211> LENGTH: 22
<212> TYPE: DNA
<213> ORGANISM: Artificial Sequence
<220> FEATURE:
<223> OTHER INFORMATION: Reverse Primer bax-2 reverse

<400> SEQUENCE: 18
tctgaaacaa ttctgggtag gc                                            22

<210> SEQ ID NO 19
<211> LENGTH: 18
<212> TYPE: DNA
<213> ORGANISM: Artificial Sequence
<220> FEATURE:
<223> OTHER INFORMATION: Forward Primer bad-1 forward

<400> SEQUENCE: 19
agatcccgct cagctcct                                                 18

<210> SEQ ID NO 20
<211> LENGTH: 24
<212> TYPE: DNA
<213> ORGANISM: Artificial Sequence
<220> FEATURE:
<223> OTHER INFORMATION: Reverse Primer bad-1 reverse

<400> SEQUENCE: 20
ttcctgcact ttttactctc ttca                                          24

<210> SEQ ID NO 21
<211> LENGTH: 23
<212> TYPE: DNA
<213> ORGANISM: Artificial Sequence
<220> FEATURE:
<223> OTHER INFORMATION: Forward Primer bok-1 forward

<400> SEQUENCE: 21
cgaaaaggtt tggaaaaaca taa                                           23
```

-continued

<210> SEQ ID NO 22
<211> LENGTH: 20
<212> TYPE: DNA
<213> ORGANISM: Artificial Sequence
<220> FEATURE:
<223> OTHER INFORMATION: Reverse Primer bok-1 reverse

<400> SEQUENCE: 22
ccgaacacag tccacagcta                                              20

<210> SEQ ID NO 23
<211> LENGTH: 19
<212> TYPE: DNA
<213> ORGANISM: Artificial Sequence
<220> FEATURE:
<223> OTHER INFORMATION: Forward Primer bok-2 forward

<400> SEQUENCE: 23
gtgccatggc tcaaaaga                                                19

<210> SEQ ID NO 24
<211> LENGTH: 24
<212> TYPE: DNA
<213> ORGANISM: Artificial Sequence
<220> FEATURE:
<223> OTHER INFORMATION: Reverse Primer bok-2 reverse

<400> SEQUENCE: 24
gagtccatgt ttaccacaca tttt                                         24

<210> SEQ ID NO 25
<211> LENGTH: 22
<212> TYPE: DNA
<213> ORGANISM: Artificial Sequence
<220> FEATURE:
<223> OTHER INFORMATION: Forward Primer ef-1alpha forward

<400> SEQUENCE: 25
cctctttctg ttacctggca aa                                           22

<210> SEQ ID NO 26
<211> LENGTH: 21
<212> TYPE: DNA
<213> ORGANISM: Artificial Sequence
<220> FEATURE:
<223> OTHER INFORMATION: Reverse Primer ef-1alpha reverse

<400> SEQUENCE: 26
cttttccttt cccatgattg a                                            21

<210> SEQ ID NO 27
<211> LENGTH: 24
<212> TYPE: DNA
<213> ORGANISM: Artificial Sequence
<220> FEATURE:
<223> OTHER INFORMATION: Asp mRNA detection sense

<400> SEQUENCE: 27
caataaggac acagcctcgt gatg                                         24

<210> SEQ ID NO 28
<211> LENGTH: 24
<212> TYPE: DNA
<213> ORGANISM: Artificial Sequence
<220> FEATURE:
<223> OTHER INFORMATION: Asp mRNA detection antisense

```
<400> SEQUENCE: 28
cagactgcga aacatgtgga aagg                                              24

<210> SEQ ID NO 29
<211> LENGTH: 24
<212> TYPE: DNA
<213> ORGANISM: Artificial Sequence
<220> FEATURE:
<223> OTHER INFORMATION: Odf mRNA detection sense

<400> SEQUENCE: 29
gtgaaacaga gaagaagcgt ccag                                              24

<210> SEQ ID NO 30
<211> LENGTH: 24
<212> TYPE: DNA
<213> ORGANISM: Artificial Sequence
<220> FEATURE:
<223> OTHER INFORMATION: Odf mRNA detection antisense

<400> SEQUENCE: 30
aggaagcgtg tatttgtttg gggc                                              24

<210> SEQ ID NO 31
<211> LENGTH: 24
<212> TYPE: DNA
<213> ORGANISM: Artificial Sequence
<220> FEATURE:
<223> OTHER INFORMATION: Sam mRNA detection sense

<400> SEQUENCE: 31
tatctcgcag ttggtcatgg tctg                                              24

<210> SEQ ID NO 32
<211> LENGTH: 24
<212> TYPE: DNA
<213> ORGANISM: Artificial Sequence
<220> FEATURE:
<223> OTHER INFORMATION: Sam mRNA detection antisense

<400> SEQUENCE: 32
gccgtattaa agcaacaggg aagt                                              24

<210> SEQ ID NO 33
<211> LENGTH: 21
<212> TYPE: DNA
<213> ORGANISM: Artificial Sequence
<220> FEATURE:
<223> OTHER INFORMATION: beta-actin sense

<400> SEQUENCE: 33
gtccctgtac gcctctggtc g                                                 21

<210> SEQ ID NO 34
<211> LENGTH: 21
<212> TYPE: DNA
<213> ORGANISM: Artificial Sequence
<220> FEATURE:
<223> OTHER INFORMATION: beta-actin antisense

<400> SEQUENCE: 34
gccggactca tcgtactcct g                                                 21
```

```
<210> SEQ ID NO 35
<211> LENGTH: 24
<212> TYPE: DNA
<213> ORGANISM: Artificial Sequence
<220> FEATURE:
<223> OTHER INFORMATION: Asp promoter region formard primer

<400> SEQUENCE: 35
attgtcctgt ctctacagat ttgg                                          24

<210> SEQ ID NO 36
<211> LENGTH: 33
<212> TYPE: DNA
<213> ORGANISM: Artificial Sequence
<220> FEATURE:
<223> OTHER INFORMATION: Asp promoter region antisense primer

<400> SEQUENCE: 36
cgctagcccc atcacttcac tttgagctgt gtt                                33

<210> SEQ ID NO 37
<211> LENGTH: 27
<212> TYPE: DNA
<213> ORGANISM: Artificial Sequence
<220> FEATURE:
<223> OTHER INFORMATION: Odf promter region sense primer

<400> SEQUENCE: 37
gacgaaaata ccatgctaaa ttgaccc                                       27

<210> SEQ ID NO 38
<211> LENGTH: 36
<212> TYPE: DNA
<213> ORGANISM: Artificial Sequence
<220> FEATURE:
<223> OTHER INFORMATION: Odf promoter region antisense primer

<400> SEQUENCE: 38
cgctagcccc atgaccacat ttgagaccga aggtaa                             36

<210> SEQ ID NO 39
<211> LENGTH: 27
<212> TYPE: DNA
<213> ORGANISM: Artificial Sequence
<220> FEATURE:
<223> OTHER INFORMATION: Sam promoter region sense primer

<400> SEQUENCE: 39
tacaaaaaga gacctaaaac ctagagg                                       27

<210> SEQ ID NO 40
<211> LENGTH: 36
<212> TYPE: DNA
<213> ORGANISM: Artificial Sequence
<220> FEATURE:
<223> OTHER INFORMATION: Sam promoter region antisense primer

<400> SEQUENCE: 40
cgctagcccc atggtttctg ctgtaaatga gctaag                             36

<210> SEQ ID NO 41
<211> LENGTH: 24
<212> TYPE: DNA
<213> ORGANISM: Artificial Sequence
<220> FEATURE:
<223> OTHER INFORMATION: eGFP:Ntr fusion gene detection forward primer
      G-for
```

```
<400> SEQUENCE: 41
cactacctga gcacccagtc cgcc                                              24

<210> SEQ ID NO 42
<211> LENGTH: 24
<212> TYPE: DNA
<213> ORGANISM: Artificial Sequence
<220> FEATURE:
<223> OTHER INFORMATION: eGFP:Ntr fusion gene reverse primer N-rev

<400> SEQUENCE: 42
ggatttggca acacgcgctt tacc                                              24

<210> SEQ ID NO 43
<211> LENGTH: 2211
<212> TYPE: DNA
<213> ORGANISM: Danio rerio

<400> SEQUENCE: 43
aataaatgtc tgaaacctta tctttggctt ttttttattta tttatttttta tatataaaag      60 ccttttttacc tctaaccatg ggattaaaaa caatggttaa gtcgtaatgt actataaaag      120
agaatcattc tccttaaggt taaaacgttt aagaatggct gctttagtaa aacaaactgt      180
ttcagttctc actttgcttg tattagatcc aatgtcttat gcagtaaaat atacatattt      240
ctggtcttcg cttaatttaa caactttcag ggattaactt aaattagttt acaaagaata      300
agtgtttctc ctgtcacatt ggcttaagta atattagtag ttcaggactc aaccattgac      360
tgcactcttt accaaacaat tgaaccctgg tttaacaggg caagtgatag agtcacttga      420
agtgttaaat ggtgtgtgtg cacagcattg ttggtttaca aaatcaaatg ttctgtttaa      480
ctaaatgttg tttatttatt tatttttttaa ttctcctagt gtatgtatta agtttagtac      540
tcctactgac caactttttg gttgaggttg attcttaatt tttatgttgg aaatgcagtg      600
ttaaactagt gatcgtagtg aaatgagttt ttttttgttt tttttttttt tcctccttgg      660
taggacagtt aaagggtaca gtaatttatc accttttttaa accaagttga aactgggaat      720
ttttctgttt gttagaagct gtatacttaa accttaagtc ggtttcattt atatatgtct      780
taaagaccaa taatggatca aatagtaatt taacttgaat tttttttttt cattccaaca      840
ctaacaatct aagctcagat gccttttttag atcaaaagtt tatgtagttt aaaggtgcag      900
taggtgattt tccacaatgc taacagctta gcataaatct ctgaatcaca gtccctcttc      960
tgtctagagc cacacctcaa acacgagcac cgcaaaagaa ccctcttatg ttaagtgact     1020 agtgttttgtc tggcagcatg caaaccaaac tgacatgtgt cagttccaaa gtgaatagag     1080
ttgcatggtt aaaccatata gggagaggct aggtggaata gcactatttta cttgttttgt     1140 tgttaaacta aacttaaaat ctacattcta gattctgtaa aaggtccttt atgaaaattg     1200
aaaatagtct taatctttca tcggaagatt ttagtggctg aacaacacta ctgtgaagat     1260
aaaactcatt tgtaacatcc tttgagtgaa gctaaaatgg tttaaagca gaacattacc     1320 cgtctaagag aaatcctgct gccatggtgt cttccttttt ccagcatgca aagataactc     1380
caatattgat tcaggtttta aaaaagttga ttcagcaggt ttttacagat cgctttctct     1440
ctcgaatgtg tagcccaaac agcggtctgc ggagcttcaa acaaaaggct gcgcagacgt     1500
tcaaatctgc atttgctaac agacagtctg agctacctat tggaattatg agagatgtcg     1560
gcctgactat ttaattggat gaacattgtt tagttttatg ccttacccaa aatctataaa     1620
tacatttaga tcatttactt taatcattac tattggaatg agaagacact tttaacctgc     1680
```

| | | |
|---|---|---|
| acaacaacac atgcttctgg agacaatcac ctactgcacc tttaagtaat attcagtaag | 1740 | |
| gtagggtaag gaagtaatat ccagtcttac gattcaagcc tgtcctactc tttcaaaaga | 1800 | |
| aatgcaaata taccgatgat gcataatttc acattactga agttacgctt ttgagtcact | 1860 | |
| ggattgtaat gttactattt tccccaacac tgatcatatc tacagtctgt gtaaacccag | 1920 | |
| attttatttc agattaccaa cacttaatat catgaatgaa ttgtcagttt gttgattgtt | 1980 | |
| aaatcacgaa cggccataaa ttaatctcag ttatcctatt ggctgatgac attctggaag | 2040 | |
| ctccctattg gctagtagag tttgtggacc cagagtccac aaactctaca tgtccagagg | 2100 | |
| aggatcaaat gtaattaatt aagctggaag gggcggagcc aacctaattc tgacctgtat | 2160 | |
| aaaaggtcaa agccaagcat agatgagcat tgtggcattg agtcttcaag g | 2211 | |

<210> SEQ ID NO 44
<211> LENGTH: 2021
<212> TYPE: DNA
<213> ORGANISM: Danio rerio

<400> SEQUENCE: 44

| | | |
|---|---|---|
| gcttttattt tagctcataa aacgagtaag actaactaaa aaaagaata ttataggaaa | 60 | |
| taatgtgaaa aattccttgc actattaaac aacaataata ataataataa taataataat | 120 | |
| aataataatt tgggaaatat ttgaaagaaa aaaaatcaca gaagggcgaa taattttgac | 180 | |
| ctcaattgtg tacgtgtata tataatgaaa agtaactaac tatttaattg agtaattttt | 240 | |
| taatcagatt ttttttacgct tactcaagta acttttaaga tgttactttt actggagtgt | 300 | |
| agattttgta tactccaccc acctctgacg aagctctcga gggattggaa tgacatgaga | 360 | |
| gagactaatt gatgacagat gttcatttct gagtgaacta acccttttaag tcatggatcc | 420 | |
| ccaatcaatg tgttgtcatg aaagagttcc tgcaggccgc aagaatgcaa aatgactgta | 480 | |
| tatgcagtcc caccttattt cctttctaat gctgggttca cacctaagaa gcgctgcatc | 540 | |
| actctccaca gtttattaac gggatatttt cacctaatgc ttcataattg ctctggtata | 600 | |
| attatctaaa ctgtcacagt agacagttct gcatgatttc gacaagcgtg cagtttgcgt | 660 | |
| tgactttgta tgtaatctac ttgtggcagt acttcatttt tctcttgtat tggtgtgaac | 720 | |
| ccatcatgag attcagcttg tgcagcatga gcggggaaat tgatttgatt gttccaggga | 780 | |
| aacaagctaa cactgaatgt tatggtgaat tattttgggt tggcttgttg ttgcatgcgt | 840 | |
| gatatagacg tagcttcaaa tcaaactctt gttctaaatt gtaagttctt gactatttct | 900 | |
| cagcaccact cattccccca gtgtgagact aaacgatcac caagactggt ccaggcatta | 960 | |
| ttaattctga ctgcacactc ttttctcaaa ccacttttag gttaaggtgt taagaataa | 1020 | |
| taagggcaaa tagactaaaa caaaaggctt ctttactgac tctgatgtcc tctgctggtg | 1080 | |
| gaatactgac agtgcactgc atcagatcac caagtgtata tgtatgcaaa cagactccca | 1140 | |
| gaggcacaac cgagaggtca agagtgtttc aaatctgttg tgtctactag aaggtttgta | 1200 | |
| ttggtcagga tgtggtcagt tctctgtgtg ttaggccatg gtgctgatac tcaaatataa | 1260 | |
| acaacagcat ggactgcact ctttattgac cataatctga ctgtttacgc atggagaaag | 1320 | |
| cataaggaag ctgctcaatc aaacagaaag tgactttgtc aaaatatcac accagttcct | 1380 | |
| gctaactaaa tttaatagct ggtaaaaaca atgtctgagc agcattcatg aggatattag | 1440 | |
| tctaatattt ccacgtattg agtgtaaatg ataagaacac acatgaaagt tgtcagtagt | 1500 | |
| cttgctctgg aaaacctgct tcaggtttgc cttttgttcc tcagtgttta atgtcttttc | 1560 | |

```
tgcatgatat gatgtccatt ttgcagtcta aatactctg attattacag cctaaaacat    1620
gacaataact gatcattttc agctgaaata atcaccataa tatgctagct tcatttggtt    1680
tagagcaggc atgtccaaac tcagtcctgg agggccggtg tcctgcagag tctatgtatg    1740
gagatctcag tgcaaaatgg aacagattca acaagtgagc aacaaaacat tgcattagtc    1800
aaaaacatga agtatctgac taattggatt caggaaatgc cacatgctta gaacattgag    1860
aaccaataag aatccggcag agcataagct cccactagtg caagtctgga gaatcatgac    1920
tcctaatgaa gagggcggga tcatcgttaa gctaattgac ctctgtagag tacaaaaagg    1980
ccaaagggca acatctcagc agtgcatcta gctggtgaac a                        2021
```

<210> SEQ ID NO 45
<211> LENGTH: 720
<212> TYPE: DNA
<213> ORGANISM: Aequorea victoria

<400> SEQUENCE: 45

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 46
<211> LENGTH: 654
<212> TYPE: DNA
<213> ORGANISM: Escherichia coli

<400> SEQUENCE: 46

```
atggatatca tttctgtcgc cttaaagcgt cattccacta aggcatttga tgccagcaaa     60
aaacttaccc cggaacaggc cgagcagatc aaaacgctac tgcaatacag cccatccagc    120
accaactccc agccgtggca tttttattgtt gccagcacgg aagaaggtaa agcgcgtgtt    180
gccaaatccg ctgccggtaa ttacgtgttc aacgagcgta aatgcttga tgcctcgcac    240 gtcgtggtgt tctgtgcaaa aaccgcgatg acgatgtct ggctgaagct ggttgttgac    300
caggaagatg ccgatggccg ctttgccacg ccggaagcga agccgcgaa cgataaggt    360 cgcaagttct tcgctgatat gcaccgtaaa gatctgcatg atgatgcaga gtggatggca    420
aaacaggttt atctcaacgt cggtaacttc ctgctcggcg tggcggctct gggtctggac    480
gcggtaccca tcgaaggttt tgacgccgcc atcctcgatg cagaatttgg tctgaaagag    540
aaaggctaca ccagtctggt ggttgttccg gtaggtcatc acagcgttga agattttaac    600
gctacgctgc cgaaatctcg tctgccgcaa aacatcacct taaccgaagt gtaa           654
```

<210> SEQ ID NO 47
<211> LENGTH: 2178
<212> TYPE: DNA
<213> ORGANISM: Danio rerio

<400> SEQUENCE: 47

```
ttgattgtcc tgtctctaca gatttggtaa gtgagcgact agtggtcttt gtttgtttat        60
tcagaggcct aacctagtta tcctaattaa cctagttaag cttttaaatg tcactttaag       120
ctgcataaaa gtgtcattaa aaatatctag taaaatatta tttactgtca tcatggcaaa       180
gataaaataa atcagttatt agaaatgagt tattaaaact attgtgttta gaaatgtctt       240
ctctccctta accaaaaatt ggggaaaaaa taaacgggtt tatggaataa aatcactgtc       300
ataaatattt tgtgcgtaaa taaatattcc ataggggttc taataattca gggggctaa       360
taattctgac ttcaactcta tgcacagtat aaatatgatc cattcttcaa ctacgggcac       420
ttttagcctt gtgaagttga gtaaaaaaaa aacctgttca aaattaacgt aatagcctca       480
aaagttttaaa caatttgtct agttttaaga tctgtaagag tacaaaattg gataagaaga       540
gaaacatttt tctcatcgtg aactgaaaat gtcatttcca ccacatctta gtatacagct       600
tttatttcaa aatttaataa acttttccac aatatgtata caatggggta tatgccaaag       660
catgcaaata ggacttttaa tttgccagta acctgggtta agcgcttccg gcgaattgaa       720
tgccaatgca aaatccgtgc gtttaaggta tgttttcttt aaagatgagc gatctccact       780
agctgagtga tgtccgattt aaagtgggtc tcagattgta caagaagcac tgcattaaat       840
tacatttccc ctgccatgtc tttataatat gagcatttat tttaccccag tatattcaat       900
ggagcttctg tgttagcctg ccgattctga caggcgcgtg cgagtaaaca gcttttttgtc       960
tcgttttacg cttgagcaac caaataaatg ctaacgttta tttaactgaa tgtatttaa      1020
tgacattaca acatcgatgc tgtataagga accgtataaa atggaaaaaa gttcacaata      1080
acaggtcacc agaagtgtat cagcatggat acagcactag ctcggcttat accctattat      1140
acatttgtta ataaaataaa ttagttgtat gctgaatttt tcacctgtca ccctctacaa      1200
tttaatatta ttttggttaa gagcttatga gaaaataaaa taaactgaat ttgtataata      1260
aataaagcat gaacttatac attgtgaata cacttttaat gtgtgaagag agcttttttaa      1320
aaaaaattaa aaatgagagt ggtgatggaa atgacagtgg tggaaatggc atttcaacag      1380
tttattgtga aaaaatgaaa aatatcttca ccgattaggt ttgaattgat tctagccttt      1440
catgtataca aaacactctt atttatcttc attttgcttg gttttttaaaa acaactttaa      1500
agggatctcc acaggatacg caatgctaca ataaatacgc aacctttttat aagcggaaac      1560
ctacatatat tcggaggaca tggcaacaac agctgtagtt aacgcccttt atttgacatt      1620
gaccaatcag atcacaaaga gctctttcgg cgtctaggtg acgcttccaa acaacacgtt      1680
gctatgaaaa acagaacaag tcgctgctgc attttaggat gccaaaaaac tatatataat      1740
actattaata gtatattttc tataaagtac taactattat attaataaaa cgacataatc      1800
gcatctcttt atttaaaata acataacggt aagtctggat aatagataga gttaactttta      1860
gcacgtacgt ttttgtataa cgttaatgta ctgtatgtaa cgtatttttct ttaatcatgt      1920
tttagtgtta tgtgacatga aatatgctga tatggccttt cccgttttgc atgtattgaa      1980
ttcatgctat ttcactttttt atatatattg taacatatat tgtattaata acttttttgt      2040
gtgtgcagtt tctcttttctt atcctaaaac acagctcaaa gtgaagtgat gcctcttttca      2100
gaaaccatgt actgcgctca gcagatcaac atccctccag ctctgcccaa tatgttaaag      2160
cagttcacta aagcagca                                                    2178
```

<210> SEQ ID NO 48
<211> LENGTH: 2079
<212> TYPE: DNA
<213> ORGANISM: Danio rerio

<400> SEQUENCE: 48

```
cagcttgtac aacttttgaa aaggaaccac cccagtgaca gcttgcgtaa ctttgtttct      60
gagaatgtac acaaactgga atataatttg tacagaatat aagctatttt gacgaaaata     120
ccatgctaaa ttgacccttt attgggcact cattgaaata ctacaaaata ccaaaaccat     180
ggaaagttat tgagggttag aagacttcta tgattttaaa acactaattt taagtaggaa     240
atcaaggtca atgaagttac catatttgat ttttttttatc cattaaaagg gtaaaattga    300
tagcacctaa aaaatctgca tcatgatcat taaattaata atacattttg gttcatttca     360
ctgtgtatcc aggtataaaa gagtgatttt aatatcattt actgtattga aagttccatt     420
aaataaatga taaaaatgca tattctgcaa agtattctgc ctatgtaaat tttgaaaatt     480
aatgtcaaaa gcgaaacatt tagaaaacaa tgaacagaaa tacattttaa tgcaatctgt     540
attgtgtgaa atgtttgttt tgcaatgctt gaatttcaat ttgcatacaa tatgaccttg     600
tttctatttta ccgatgttat ctaaaacagg gattcccaat ctttaaagcc cgcaacccct    660
aaaataagaa gactcgcgac acccaaattc ctcctaggtg gttatacata tgcaaacgtt     720
gctcatacaa cattaggcct atataaacat gagcatattg acaactagag atggctaaag     780
tacacacacc ctttactaaa gtagaagcac agacactcat gtttaaaatg tttctggcaa     840
aagttgaagt accgactaca catttgtact caagtataag taaagcagta cggcctaaaa     900
catgtactta agtaaaaagt attcattact agtacctgtt ttagtttcac agtgctaact     960
acggcacatc aggtatacat ctactatttta ggatggatac tttgcgaatt ggaatgcagc   1020
agaagtttct ttatggacta aaaacactgt tacgtccagt gttgccaccc tgtggacaaa    1080
ctaattaatg aaaaaaatca agatgctgta tacgggttaa agtagcaggc aatctgttga    1140
cccccattta gcttcaagct cttttaagca agcgtgaagt tcctagcaac acattgaccc    1200
catgtgttgc atgttggcat ttacctctgg ttaccatagc atcaggctta acagttaatg    1260
tttaatgttt tttttctggt taatgcagta ggtggatata tctaccatac ctacaactcg    1320
caatttatat gcactcagaa ttttgacaca atgcttttca tgtgcatata agaaaatata    1380
gtacgcactc ttctagatgt tcatctcttc taaaatatta agggcccact ttatacagct    1440
ttgcaggagg cccccaggt gctggtctcc ctggtgaccc atgcttgatg gtccatctct     1500
ggcctgtaaa ggcatgaaag ggaattgagg ggagggatta gcctacctga tggagataat    1560
gttacaccac gatgaattca agtgatgaca tctttgtgct tctgtctctc atatgcgtgt    1620
gtatatttaa tgggtttggt ggcccctgac tgagtccacc agcttgaatg aagattacac    1680
caaactgttc gttttttctga tttaagtgac ggctgtaatt atgacatcat cagatggagg    1740
accatggaga acttgactga acttgtccag tccaaatgag gtcaggactt ttttacagtg    1800
gacatcagat tttcgccgga aggacgaaaa cgacacctgt ttcagcttct tgggtttttt    1860
taattgctta aaaaagctaa tgctgaggta aaagctaaat ccttaatagc tgctctttga    1920
gcttggttta ctcaaatttt atgaaagttg tcatagggac ttgataaggt ctacggctga    1980
ctatgcagca aacatagtaa gcaaagactt ttaccttcgg tctcaaatgt ggtcatgact    2040
atgagtgaaa cagagaagaa gcgtccagtc attgctggc                           2079
```

<210> SEQ ID NO 49
<211> LENGTH: 2079
<212> TYPE: DNA
<213> ORGANISM: Danio rerio

<400> SEQUENCE: 49

```
ttagattaat attttacaa aagagacct aaaacctaga ggaaaattat tttgtaatgt      60
ttattttgaa gatattgtgt ggagaaaaga ttggttgatt cctttcagt cctgcatagg    120
taataaatag aggcaactac atttaaacat tttacacaac atttatgtta gcaattacac   180
attaactaaa ttatgcagac tggtggaaac tgttcaatct gtttacatca ctcaaaatct   240
ttgattcctc tttttatga atgtgaatgt aacgaaaggt ctgacacaga gggatcaatt    300
tgcagtatat ttattaaaca cagtttaata aaaagcacac agtatgcact agtgtgcgaa   360
cttaaatcaa tcacagatgt atagggtcga taggctggcg caggcataca cagggtgata   420
tagcaggcat gggtcagagg caggcggtta ggatcaatgt cgatattcag ctgggttca    480
agacaggtag caggcaaggc aaggcaaggc aaggcaaggc aaggcaaggc aaggcaaggc   540
aaggccaagg tccaggttag caacagggag atcaggtaag gatgaaaacc gctcagcaat   600
gttaacagag gcagaacaag acttcgcact ggagcgtatg tttgggctgc ttatatgtgt   660
gcgtgggtaa tcagtgtgat gtggaccagg tgtgtggcaa tcagtgtctg agagggtgac   720
gtaatgtcag tagtgcggtg atgatgacct ctgctggcca gcgaggagaa tgactgggac   780
cgagtcagtg acagagaaca attaaaaaaa aacttgggaa gatctatcat tgtatgtcca   840
aaaaaaatca ggttttagtt gtaacttaac ccccaacgat gttatttaat tatttatttt   900
tttattcatt tatttatta tttattat tattcattca ttcattcatt tttgtttcaa     960
actatttatc tgtggaattt atgatgaatc ttttaattta atttaatttt tattgtatgt  1020
taaatgcaga ttaaataact ctaaaccttg tttaaatgtt gctattatag attttcattt  1080
gtatatagaa tcgctccaaa atattaatag cgaaaaatgt aaaaataaaa ttatagtggc  1140
aaaggagctg aagttaattg actagtaaac ttgctgttat ttgtataggt taaaataata  1200
tcattgtaaa gatctctttg ttgaactgtt ttttatttat ttaatttatg tatttttt   1260
gtttattttt acttttgttt atagttactt ttgtatttt tggatgtcat gtttaaattg  1320
tatatttgct gttgtttaat ttaaaaaaaa aaaacatatt tgtacccatc tgttctcaac  1380
agaagtgaga attggcgtat catatgcaca caaaaatgga atttggcgta tgcattgcac  1440
gcaaagggaa agtgtaaagt catgttattt gtacgcatat tgatgagatc gggttgaata  1500
aaatatgaaa ataacttaca caaaagtttt tgataagatt ctcgtttggt tataaaaatc  1560
agctagaacc tagagggaag ttctctgtgg gtaatgacca tcgaaaataa tctgtaagga  1620
acgttttgga aagttggacg ttttccaaac gcgaaccatt tgaagattgt gtttgcaggg  1680
atgccgcaat caggttgttt ataagaggtg ttgctgagca atttatgttt tttacaaata  1740
aaataatcac atatatttaa agctttaaat tcttctcacg tgtacttagc gtatatatga  1800
tgctaatttc gagttcaaaa actaatatcg aattaatatt atttggaaat atgcgtaatt  1860
gccaccgcgc cctggagtct cttgtaacct ctgttggtgt ttcattgcct tccgtcttcg  1920
gaagactgcc gggcgttccc tgggagtata aatctagcgg atctaacagg agtctgacag  1980
cagtgtaacg gtcttctact tgaacttagc tcatttacag cagaaaccat gaacaaaatc  2040
attttcggct ccttttgtgct cgctctttat ctcgcagtt                        2079
```

```
<210> SEQ ID NO 50
<211> LENGTH: 33
<212> TYPE: DNA
<213> ORGANISM: Artificial Sequence
<220> FEATURE:
<223> OTHER INFORMATION: Forward Primer KR(f)

<400> SEQUENCE: 50
actaccggta tgctgtgctg tatgagaaga acc                                    33

<210> SEQ ID NO 51
<211> LENGTH: 34
<212> TYPE: DNA
<213> ORGANISM: Artificial Sequence
<220> FEATURE:
<223> OTHER INFORMATION: Reverse Primer KR (r)

<400> SEQUENCE: 51
actatcgatt taatcctcgt cgctaccgat ggcg                                   34

<210> SEQ ID NO 52
<211> LENGTH: 24
<212> TYPE: DNA
<213> ORGANISM: Artificial Sequence
<220> FEATURE:
<223> OTHER INFORMATION: Forward Primer KR-id (f)

<400> SEQUENCE: 52
atgctgtgct gtatgagaag aacc                                              24

<210> SEQ ID NO 53
<211> LENGTH: 25
<212> TYPE: DNA
<213> ORGANISM: Artificial Sequence
<220> FEATURE:
<223> OTHER INFORMATION: Reverse Primer KR-id (r)

<400> SEQUENCE: 53
ttaatcctcg tcgctaccga tggcg                                             25

<210> SEQ ID NO 54
<211> LENGTH: 774
<212> TYPE: DNA
<213> ORGANISM: Aequorea victoria

<400> SEQUENCE: 54
atgctgtgct gtatgagaag aaccaaacag gttgaaaaga tgatgagga ccaaaagatc        60 tccgagggcg cccccgccct gttccagagc gacatgacct tcaaaatctt catcgacggc      120
gaggtgaacg gccagaagtt caccatcgtg gccgacggca gcagcaagtt ccccacggc       180 gacttcaacg tgcacgccgt gtgcgagacc ggcaagctgc ccatgagctg gaagcccatc      240
tgccacctga tccagtacgg cgagcccttc ttcgcccgct accccgacgg catcagccat      300
ttcgcccagg agtgcttccc cgagggcctg agcatcgacc gcaccgtgcg cttcgagaac      360
gacggcacca tgaccagcca ccacacctac gagctggacg acacctgcgt ggtgagccgc      420
atcaccgtga actgcgacgg cttccagccc gacggcccca tcatgcgcga ccagctggtg      480
gacatcctgc caacgagac ccacatgttc cccacggcc caacgccgt gcgccagctg        540 gccttcatcg gcttcaccac cgccgacggc ggcctgatga tgggccactt cgacagcaag      600
atgaccttca acggcagccg cgccatcgag atccccggcc acacttcgt gaccatcatc       660
```

```
accaagcaga tgagggacac cagcgacaag cgcgaccacg tgtgccagcg cgaggtggcc    720
tacgcccaca gcgtgccccg catcaccagc gccatcggta gcgacgagga ttaa          774
```